US011193118B2

(12) United States Patent
Dorfman et al.

(10) Patent No.: US 11,193,118 B2
(45) Date of Patent: Dec. 7, 2021

(54) MOLECULAR FILTER

(71) Applicant: Regents of the University of Minnesota, Minneapolis, MN (US)

(72) Inventors: Kevin David Dorfman, Edina, MN (US); Pranav Agrawal, Minnepolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 175 days.

(21) Appl. No.: 16/135,737

(22) Filed: Sep. 19, 2018

(65) Prior Publication Data

US 2019/0085321 A1 Mar. 21, 2019

Related U.S. Application Data

(60) Provisional application No. 62/560,489, filed on Sep. 19, 2017.

(51) Int. Cl.
*C12N 15/10* (2006.01)
*G01N 1/40* (2006.01)

(52) U.S. Cl.
CPC ....... *C12N 15/1017* (2013.01); *G01N 1/4077* (2013.01); *G01N 2001/4088* (2013.01)

(58) Field of Classification Search
CPC ............ C12N 15/1017; G01N 1/4077; G01N 2001/4088
See application file for complete search history.

(56) References Cited

U.S. PATENT DOCUMENTS

2007/0090026 A1* 4/2007 Han ............... B01D 61/027
209/2
2014/0272958 A1* 9/2014 Ramsey ........... B01L 3/502715
435/6.11

FOREIGN PATENT DOCUMENTS

WO WO 2016/182811 11/2016

OTHER PUBLICATIONS

Agrawal et al., "Entropic Trap Purification of Long DNA," Lab on a Chip, vol. 18, Feb. 2018, 15 pp.
Agrawal et al., "Fast, Efficient, and Gentle Transfection of Human Adherent Cells in Suspension," Applied Materials & Interfaces, vol. 8, No. 14, Apr. 2016, 5 pp.
Agrawal et al., "Tunable Short-Pass Filter for Recovering Long DNA Using Entropic Traps," Poster submitted at National Institutes of Health, Sep. 20, 2016, 1 pp.

(Continued)

*Primary Examiner* — Dirk R Bass
(74) *Attorney, Agent, or Firm* — Shumaker & Sieffert, P.A.

(57) ABSTRACT

A molecular filter that may include a substrate. The substrate may define a first channel, a second channel, at least one slit fluidically coupling the first channel to the second channel, at least one inlet port fluidically coupled to the first channel, at least one recovery port fluidically coupled to the first channel, at least one purge port fluidically coupled to the first channel, and at least one filtrate port fluidically coupled to the second channel. A respective cross-sectional area of each respective slit of the at least one slit in a plane perpendicular to a long axis of the respective slit is smaller than a cross-sectional area of the first channel in a plane perpendicular to a long axis of the first channel.

14 Claims, 23 Drawing Sheets

(56) References Cited

OTHER PUBLICATIONS

Alabert et al., "Chromatin Dynamics During DNA Replication and Uncharacterized Replication Factors Determined by Nascent Chromatin Capture (NCC) Proteomics," Nature Cell Biology, vol. 16, No. 3, Mar. 2014, 27 pp.
Alabert et al., "Chromatin Replication and Epigenome Maintenance," Nature Reviews Molecular Cell Biology, vol. 13, Mar. 2012, 15 pp.
Alabert et al., "Two Distinct Modes for Propagation of Histone PTMs Across the Cell Cycle," Genes & Development, vol. 29, Feb. 2015, 7 pp.
Ask et al., "Codanin-1, Mutated in the Anaemic Disease CDAI, Regulates Asf1 Function in S-phase Histone Supply," The EMBO Journal, vol. 31, No. 8 (Correction in vol. 31, No. 14), Jul. 2012, 12 pp.
Berger et al., "Light-emitting Self-assembled Peptide Nucleic Acids Exhibit Both Stacking Interactions and Watson-Crick Base Pairing," Nature Nanotechnology, vol. 10, Mar. 2015, 8 pp.
Berman et al., "Regions of Focal DNA Hypermethylation and Long-range Hypomethylation in Colorectal Cancer Coincide with Nuclear Lamina-associated Domains," Nature Genetics, vol. 44, No. 1, Jan. 2012, 17 pp.
Bogas et al., "Applications of Optical DNA Mapping in Technology," BioTechniques, vol. 62, No. 6, Jun. 2017, 11 pp.
Byk et al., "Matrix-assisted Peptide Synthesis on New Biocompatible Nanoparticles," Monographic Special Issue Oligos & Peptides, Chimica Oggi, Chemistry Today, vol. 33, No. 2, Mar. 2015, 4 pp.
Cheong et al., "Wall Depletion Length of a Channel-confined Polymer," Physical Review E, vol. 95, Feb. 2017, 20 pp.
Dai et al., "Revisiting Blob Theory for DNA Diffusivity in Slitlike Confinement," Physical Review Letters, vol. 110, No. 6, Apr. 2013, 10 pp.
Dorfman et al., "Beyond Gel Electrophoresis: Microfluidic Separations, Fluorescence Burst Analysis, and DNA Stretching," Chemical Reviews, vol. 113, No. 4, Apr. 2013, 84 pp.
Dorfman, "DNA Electrophoresis in Microfluidic Post Arrays Under Moderate Electric Fields," Physical Review E, vol. 73, No. 6, Jun. 2006, 10 pp.
Feng et al., "BRPF3-BO1 Regulates Replication Origin Activation and Histone H3K14 Acetylation," The EMBO Journal, vol. 35, Jan. 2016, 17 pp.
Fu et al., "A Patterned Anisotropic Nanofludic Sieving Structure for Continuous-flow Separation of DNA and proteins," Nature Nanotechnology, vol. 2, No. 2, Feb. 2007, 17 pp.
Fu et al., "Molecular Sieving in Periodic Free-energy Landscapes Created by Patterned Nanofilter Arrays," Physical Review Letters, vol. 97, No. 1, Jul. 2006, 9 pp.
Gabrieli et al., "Cas9-Assisted Targeting of Chromosome Segments (CATCH) for Targeted Nanopore Sequencing and Optical Genome Mapping," BioRxiv, Feb. 2017, 11 pp.
Gallina et al., "Cmr1/WDR76 Defines a Nuclear Genotoxic Stress Body Linking Genome Integrity and Protein Quality Control," Nature Communications, vol. 6, Mar. 2015, 16 pp.
Garcia-Lopez et al., "Synthesis and Photostability of Unimolecular Submersible Nanomachines: Toward Single-Molecule Tracking in Solution," Organic Letters, vol. 18, No. 10, May 2016, 4 pp.
Gilboa et al., "Single-Molecule DNA Methylation Quantification Using Electro-optical Sensing in Solid-State Nanopores," ACS Nano, vol. 10, Aug. 2016, 10 pp.
Grunwald et al., "Bacteriophage Strain Typing by Rapid Single Molecule Analysis," Nucleic Acids Research, vol. 43, No. 18, May 2015, 8 pp.
Grunwald et al., "Reduced Representation Optical Methylation Mapping (R2OM2)," bioRxiv, Mar. 2017, 21 pp.
Gupta et al., "Experimental Evidence of Weak Excluded Volume Effects for Nanochannel Confined DNA," ACS Macro Letters, vol. 4, Jul. 2015, 21 pp.

Gupta et al., "Mixed Confinement Regimes During Equilibrium Confinement Spectroscopy of DNA," The Journal of Chemical Physics, vol. 140, No. 21, Jun. 2014, 9 pp.
Hammond et al., "Histone Chaperone Networks Shaping Chromatin Function," Nature Reviews Molecular Cell Biology, vol. 18, No. 3, Mar. 2017, 40 pp.
Han et al., "Characterization and Optimization of an Entropic Trap for DNA Separation," Analytical Chemistry, vol. 74, No. 2, Jan. 2002, 8 pp.
Han et al., "Separation of Long DNA Molecules in a Microfabricated Entropic Trap Array," Science, vol. 288, May 2000, 5 pp.
Harnoy et al., "Enzyme-Responsive Amphiphilic PEG-Dendron Hybrids and Their Assembly into Smart Micellar Nanocarriers," Journal of the American Chemical Society, vol. 136, Feb. 2014, 4 pp.
Hoffmann et al., "TRAIP is a PCNA-binding Ubiquitin Legase that Protects Genome Stability After Replication Stress," Journal of Cell Biology, vol. 212, Jan. 2016, 13 pp.
Huang et al., "A Unique Binding Mode Enables MCM2 to Chaperone Histones H3-H4 at Replication Forks," Nature Structural & Molecular Biology, vol. 22, No. 8, Aug. 2015, 30 pp.
Huang et al., "A DNA Prism for High-Speed Continuous Fractionation of Large DNA Molecules,", Nature Biotechnology, vol. 20, Oct. 2002, 4 pp.
Jain et al., "Modeling the Relaxation of Internal DNA Segments During Genome Mapping in Nanochannels," Biomicrofluidics, vol. 10, Sep. 2016, 20 pp.
Javer et al., "Persistent Super-diffusive Motion of *Escherichia coli* Chromosomal Loci," Nature Communications, vol. 5, Article No. 3854, May 2014, 8 pp.
Javer et al., "Short-time Movement of *E. coli* Chromosomal Loci Depends on Coordinate and Subcellular Localization," Nature Communications, vol. 4, Article No. 3003, Jun. 2013, 8 pp.
Jeffet et al., "Super-Resolution Genome Mapping in Silicon Nanochannels," ACS Nano, vol. 10, No. 11, Nov. 2016, 8 pp.
Jiang et al., "Cas9-Assisted Targeting of Chromosome Segments CATCH Enables One-step Targeted Cloning of Large Gene Clusters," Nature Communications, vol. 6, Article No. 8101, Sep. 2015, 8 pp.
Jo et al., "A Single-molecule Barcoding System Using Nanoslits for DNA Analysis," Proceedings of the National Academy of Sciences USA (PNAS), vol. 104, No. 8, Feb. 2007, 6 pp.
Khandadash et al., "Novel Biocompatible Hydrogel Nanoparticles: Generation and Size-Tuning of Nanoparticles by the Formation of Micelle Templates Obtained from Thermo-Responsive Monomers Mixtures," Journal of Nanoparticle Research, vol. 16, Dec. 2014, 18 pp.
Kim et al., "Enzymatically Incorporated Genomic Tags for Optical Mapping of DNA-Binding Proteins," Angewandte Chemie, vol. 51, No. 15, Apr. 2012, 9 pp.
Klimovskaia et al., "Tousled-like Kinases Phosphorylate Asf1 to Promote Histone Supply During DNA Replication," Nature Communications, vol. 5, Mar. 2014, 13 pp.
Levy-Sakin et al., "Beyond Sequencing: Optical Mapping of DNA in the Age of Nanotechnology and Nanoscopy," Current Opinion in Biotechnology, vol. 24, No. 4, Aug. 2013, 9 pp.
Levy-Sakin et al., "Towards Single-Molecule Optical Mapping of the Epigenome," ACS Nano, vol. 8, No. 1, Jan. 2014, 21 pp.
Long et al., "Measuring Bacterial Adaptation Dynamics at the Single-cell Level Using a Microfluidic Chemostat and Time-lapse Fluorescence Microscopy," Analyst, vol. 139, No. 20, Aug. 2014, 9 pp.
Long et al., "Microfluidic Chemostat for Measuring Single Cell Dynamics in Bacteria," Lab on a Chip, vol. 13, Feb. 2013, 8 pp.
Marziali et al., "Novel Electrophoresis Mechanism Based on Synchronous Alternating Drag Perturbation," Electrophoresis, vol. 26, Jan. 2005, 9 pp.
Mejlvang et al., "New Histone Supply Regulates Replication Fork Speed and PCNA Unloading," The Journal of Cell Biology, vol. 204, No. 1, Dec. 2013, 15 pp.
Meltzer et al., "A Lab-on-chip for Biothreat Detection Using Single-Molecule DNA Mapping," Lab Chip, vol. 11, Feb. 2011, 11 pp.

(56) References Cited

OTHER PUBLICATIONS

Michaeli et al., "Channeling DNA for Optical Mapping," News and Views, Nature Biotechnology, vol. 30, No. 8, Aug. 2012, 2 pp.
Michaeli et al., "Optical Detection of Epigenetic Marks: Sensitive Quantification and Direct Imaging of Individual Hydroymethylcytosine Bases," Chemical Communications, vol. 49, No. 77, Jun. 2013, 3 pp.
Muralidhar et al., "Backfolding of DNA Confined in Nanotubes: Flory Theory Versus the Two-State Cooperativity Model," Macromolecules, vol. 49, Jan. 2016, 7 pp.
Muralidhar et al., "Backfolding of Wormlike Chains Confined in Nanochannels," Macromolecules, vol. 47, Nov. 2014, 42 pp.
Muralidhar et al., "Interplay Between Chain Stiffness and Excluded Volume of Semiflexible Polymers Confined in Nanochannels," The Journal of Chemical Physics, vol. 140, No. 8, Feb. 2014, 12 pp.
Muralidhar et al., "Kirkwood Diffusivity of Long Semiflexible Chains in Nanochannel Confinement," Macromolecules, vol. 48, No. 8, Apr. 2015, 25 pp.
Muralidhar et al., "The Backfolded Odijk Regime for Wormlike Chains Confined in Rectangular Nanochannels," Polymers, vol. 8, No. 3, Mar. 2016, 15 pp.
Nifker et al., "One-Pot Chemoenzymatic Cascade for Labelling of the Epigenetic Marker 5-Hydroxymethylcytosine," Chembiochem, vol. 16, No. 13, Sep. 2015, 5 pp.
Reifenberger et al., "Topological Events in Single Molecules of *E. coli* DNA Confined in Nanochannels," Analyst, vol. 140, No. 14, Jul. 2015, 17 pp.
Reinhart et al., "Distribution of Distances Between DNA Barcode Labels in Nanochannels Close to the Persistence Length," The Journal of Chemical Physics, vol. 142, No. 6, Feb. 2015, 10 pp.
Saredi et al., "H4 K20me0 Marks post-Replicative Chromatin and Recruits the TONSL-MMS22L DNA Repair Complex," Nature, vol. 534, Jun. 2016, 27 pp.
Shahal et al., "Simple and cost-effective fluorescent labeling of 5-hydroxymethyl cytosine," Methods and Applications in Fluorescence, vol. 4, Oct. 2016, 7 pp.
Shahal et al., "Spectroscopic Quantification of 5-Hydroxymethylcytosine in Genomic DNA," Analytical Chemistry, vol. 86, No. 16, Aug. 2014, 7 pp.
Shaul et al., "Synthesis and Evaluation of Membrane Permeabilizing Properties of Cationic Amphiphiles Derived from the Disaccharide Trehalose," Organic & Biomolecular Chemistry, vol. 14, Mar. 2016, 4 pp.
Shaul et al., "The Structure of Anthracycline Derivatives Determines Their Subcellular Localization and Cytotoxic Activity," ACS Medical Chemistry Letters, vol. 4, No. 4, Feb. 2013, 6 pp.
Sheats et al., "Measurements of DNA Barcode Label Separations in Nanochannels from Time-series Data," Biomicrofluidics, vol. 9, No. 6, Nov. 2015, 12 pp.
Shendure et al., "Next-generation DNA Sequencing," Nature Biotechnology, vol. 26, No. 10, Oct. 2008, 11 pp.
St Clere Smithe et al., "Finite-size Corrections for Confined Polymers in the Extended De Gennes Regime," Physical Review E. vol. 92, No. 062601, Dec. 2015, 11 pp.
Thomas et al., "Ratchet Nanofiltration of DNA," Lab on a Chip, vol. 13, No. 18, Sep. 2013, 6 pp.
Thomas et al., "Tilted Post Arrays for Separating Long DNA," Biomicrofluidics, vol. 8, No. 3, May 2014, 11 pp.
Torchinsky et al., "Sizing Femtogram Amounts of dsDNA by Single-molecule Counting," Nucleic Acids Research, vol. 44, No. 2, Jan. 2016, 6 pp.
Tree et al., "Extension of DNA in a Nanochannel as a Rod-to-Coil Transition," Physical Review Letters, vol. 110, No. 20, May 2013, 11 pp.
Tree et al., "Mobility of a Semiflexible Chain Confined in a Nanochannel," Physical Review Letters, vol. 108, No. 22, Jun. 2012, 8 pp.
Tree et al., "Modeling the Relaxation Time of DNA Confined in a Nanochannel," Biomicrofluidics, vol. 7, No. 5, Sep. 2013, 11 pp.
Wong et al., "Scaling theory of Polymer Translocation into Confined Regions," Biophysical Journal, vol. 95, Oct. 2008, 9 pp.
Wu et al., "Fluctuations of DNA Mobility in Nanofluidic Entropic Traps," Biomicrofluidics, vol. 8, No. 4, Jul. 2014, 15 pp.
Xu et al., "Stable, Compact, Bright Biofunctional Quantum Dots with Improved Peptide Coating," Journal of Physical Chemistry B, vol. 116, No. 36, Sep. 2012, 19 pp.
Yevnin et al., "Independent and Simultaneous Three-dimensional Optical Trapping and Imaging," Biomedical Optics Express, vol. 4, No. 10, Oct. 2013, 8 pp.
Zirkin et al., "Lighting Up Individual DNA Damage Sites by In Vitro Repair Synthesis," Journal of the American Chemical Society, vol. 136, No. 21, May 2014, 6 pp.

\* cited by examiner

MOLECULAR FILTER

This application claims the benefit of U.S. Provisional Patent Application No. 62/560,489, filed Sep. 19, 2017, the entire contents of which are incorporated by reference herein.

GOVERNMENT RIGHTS

This invention was made with government support under HG006851 awarded by National Institutes of Health. The government has certain rights in the invention.

TECHNICAL FIELD

The disclosure relates to filtering molecules, such as nucleic acids.

BACKGROUND

Genome mapping and sequencing technologies principally operate at nano/micro-scale and efficient sample preparation is crucial for successful technologies, especially for genomic DNA. One of the major problems is the disconnect between sample preparation and its use in these technologies. This disconnect requires large volume of sample preparation to efficiently and conveniently carryout preparation steps. This significantly increases technology costs.

Long chain DNA molecules are important for genome technologies such as long-read sequencing, whole-genome mapping, and cell engineering. In many situations, the long chain DNA sample is contaminated by a significant amount of small DNA that results from random shearing or biochemical processing. These small DNA fragments contribute noise to the analysis; for example, genome mapping in nanochannels requires DNA greater than 150 kbp and small DNA can create spurious signals when the small DNA overlap with the larger molecules. Gel electrophoresis is the standard method to purify long chain DNA molecules. However, gel electrophoresis is time consuming, due to the slow mobility of long chain DNA in a gel and requires a high initial DNA concentration for purification. Gel electrophoresis requires large amounts of DNA, which are not required for long-read sequencing and whole-genome mapping. Consequently, most of the DNA that comes out from the purification step may not be used. In many applications, the sample of interest is not abundant enough to be efficiently filtered with this process.

SUMMARY

Figure 1:
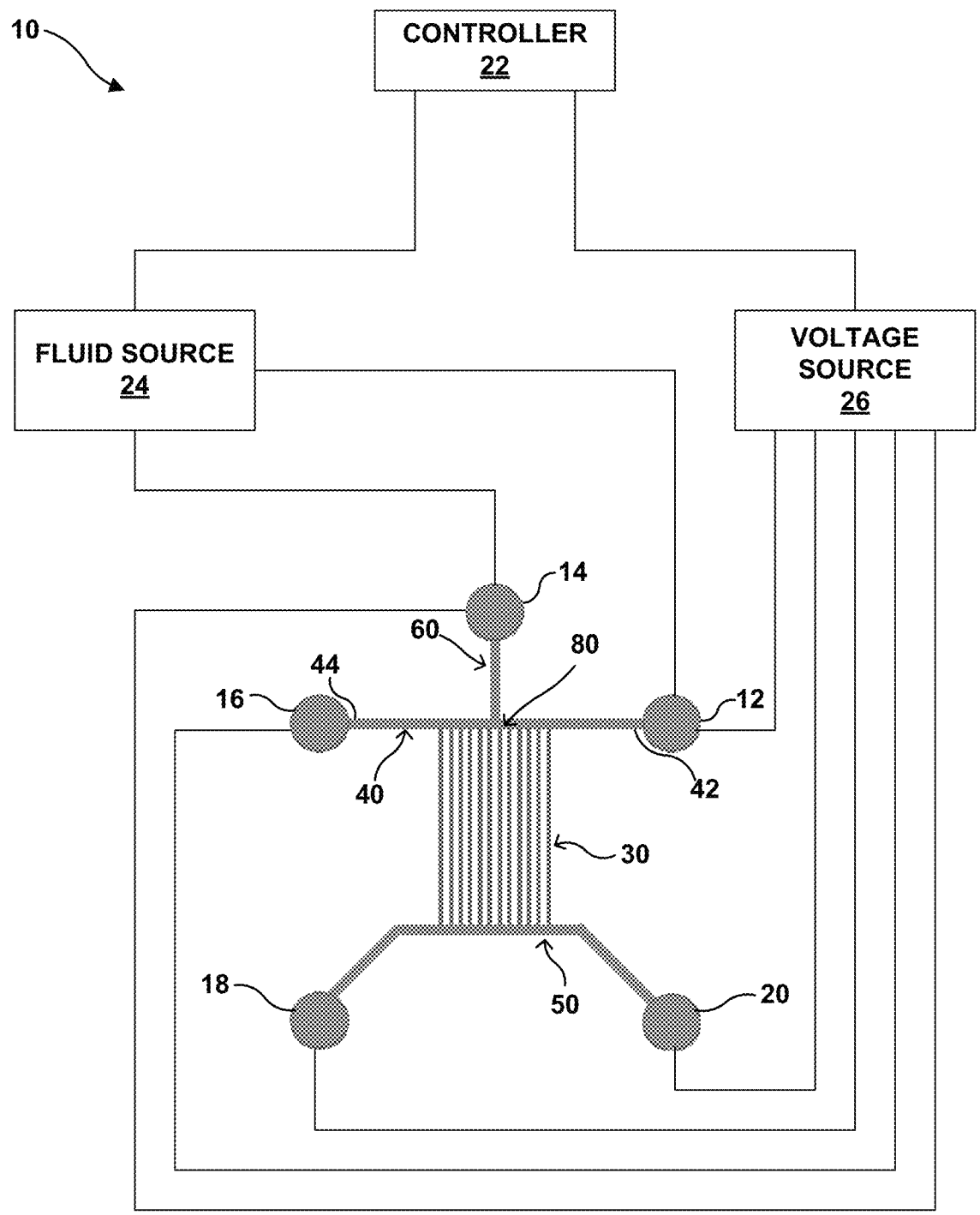
FIG. 1 is a conceptual diagram illustrating an example molecular filter device, in accordance with some examples of this disclosure.

In some examples, the disclosure describes a molecular filter that includes a substrate. The substrate may define a first channel, a second channel, at least one slit fluidically coupling the first channel to the second channel, at least one inlet port fluidically coupled to the first channel, at least one recovery port fluidically coupled to the first channel, at least one purge port fluidically coupled to the first channel, and at least one filtrate port fluidically coupled to the second channel. A respective cross-sectional area of each respective slit of the plurality of slits in a plane perpendicular to a long axis of the respective slit is smaller than a cross-sectional area of the first channel in a plane perpendicular to a long axis of the first channel.

In some examples, the disclosure describes a filter system that includes a substrate defining a first channel, a second channel, a first stage comprising at least one slit fluidically coupling the first channel to the second channel, a first purge port fluidically coupled to the first channel at or near a midpoint of the first stage, a second stage downstream of the first stage along the first channel, a second purge port fluidically coupled to the first channel at or near a midpoint of the first stage, at least one inlet port fluidically coupled to the first channel upstream of the first stage along the first channel, at least one recovery port fluidically coupled to the first channel downstream of the second stage along the first channel, and at least one filtrate port fluidically coupled to the second channel. A respective cross-sectional area of each respective slit of the first stage in a plane perpendicular to a long axis of the respective slit is smaller than a cross-sectional area of the first channel in a plane perpendicular to a long axis of the first channel. The second stage includes at least one slit fluidically coupling the first channel to the second channel. A respective cross-sectional area of each respective slit of the second stage in a plane perpendicular to a long axis of the respective slit is smaller than a cross-sectional area of the first channel in a plane perpendicular to a long axis of the first channel.

In some examples, the disclosure describes a method for using a molecular filter. The method may include, during an introduction phase, introducing a sample comprising a plurality of relatively larger molecules and a plurality of relatively smaller molecules into at least one inlet port defined in a substrate; applying no voltage to the at least one inlet port and at least one filtrate port; and applying a fixed pressure to at least one purge port defined by the substrate and the at least one inlet port to push the sample into a first channel defined by the substrate and fluidically coupled to the at least one inlet port and the at least one purge port. The method also may include, during a filtration phase, applying a substantially constant voltage between the at least one inlet port and at least one filtrate port defined by the substrate and fluidically coupled to a second channel defined by the substrate, wherein the first channel and the second channel are fluidically coupled by at least one slit; and while applying the substantially constant voltage, applying a pressure to the at least one purge port and the at least one inlet port to push relatively small molecules in the sample from the first channel through the at least one slit to the second channel to result in a filtrate in the second channel. The method additionally may include collecting a filtride of the sample remaining in the first channel from a recovery port fluidically coupled to the first channel.

The details of one or more examples are set forth in the accompanying drawings and the description below. Other features, objects, and advantages of the disclosure will be apparent from the description and drawings, and from the claims.

DETAILED DESCRIPTION

In general, the disclosure describes a molecular filter that includes a dedicated recovery port for recovering filtride while filtration is occurring. The molecular filter includes a substrate that defines a first channel, a second channel, and at least one slit fluidically connecting the first channel and the second channel. In some examples, the at least one slit includes a plurality of slits fluidically connecting the first and second channels in parallel. Interfaces between the first channel and the respective slits of the at least one slit define entropic filters, which are configured to filter molecules based on an entropic diameter (e.g., a radius of gyration) of molecules introduced to the first channel. The molecular filter also may include at least one inlet port fluidically coupled to the first channel, at least one purge port fluidically coupled to the first channel, at least one recovery port fluidically coupled to the first channel, and at least one filtrate port fluidically coupled to the second channel. The molecular filter acts like a bandpass filter, allowing most of the smaller molecules to pass through the at least one slit to the second channel while not allowing most of the larger molecules to pass through the at least one slit.

During operation, a sample including a plurality of molecules may be introduced to the at least one inlet port. The plurality of molecules may include molecules having different sizes (e.g., diameters or radii of gyration). For example, the plurality of molecules may include a plurality of nucleic acids, such as DNA, with a range of base pairs. Molecules of a selected size may be of interest for subsequent use, such as analytical methods. For example, DNA having a number of base pairs greater than a threshold number may be of analytical interest, while DNA having a number of base pairs less than the threshold number may not be analytically interesting and may, in fact, degrade a signal from the relatively long DNA molecules during subsequent analytical procedures. Thus, the molecular filter may be used to filter molecules having a selected size from other molecules.

Once the sample has been introduced in the at least one inlet port, pressure may be applied to the at least one inlet port and the at least one purge port to push the sample into the first channel. Pressure may not be applied to the at least one recovery port, the at least one filtrate port, or both.

After the sample has been introduced into the first channel, an electric field can be applied across the plurality of slits by applying an electric potential on at least one purge port, the at least one inlet port, and at least one filtrate port. The electric potential may not be applied to the at least one recovery port (e.g., the electric potential of the recovery port may be allowed to float). The system may be based on the principle that the mobility of smaller molecules across the channel-slit interface can be increased dramatically compared to mobility of larger molecules by operating at an electric field that is lower than the field strength that overcomes the entropic barrier for the larger molecules but high enough to readily allow the smaller molecules to overcome their smaller entropic barrier. In other words, the electric potential may be selected to cause movement of molecules below a selected size (e.g., entropic diameter or radius of gyration) to pass through interfaces between the first channel and the plurality of slits. In addition to the voltage, the size (e.g., height, width, or cross-sectional area) of the respective slits of the plurality of slits may be selected so that the filter passes molecules below the selected size.

While the voltage is being applied, oscillating pressure may be applied to the at least one purge port and the at least one inlet port. Pressure may not be applied to the at least one recovery port. The oscillating pressure may allow higher voltage to be used during filtration. In addition, combination of the oscillating pressure with the applied voltage may concentrate filtride molecules at different locations at the interfaces between the first channel and the plurality of slits. For example, in implementations in which a purge port is fluidically coupled to the first channel at an intermediate position of the first channel and the plurality of slits are positioned symmetrically about the purge port, the filtride molecules may concentrate at two symmetric locations of the interfaces between the first channel and the plurality of slits. Concentration of the filtride molecules may result in a more concentrated filtered sample once the filtride is recovered from the molecular filter.

In some examples, the introduction and filtrating phases or steps may be alternated, and filtride may be recovered from the at least one recovery port during the introduction steps. This may allow semi-continuous recovery of filtride molecules from the molecular filter. In this way, including the at least one recovery port, operating the molecular filter in alternating introduction and filtering phases, including oscillating pressures during the filtering phase, or combinations thereof may allow more efficient recovery of molecules of a selected size. Additionally, in some examples, a filter system may be constructed by introducing filtride from a recovery port of a first molecular filter to an input port of a second molecular filter, i.e., connecting a plurality of molecular filters in series. In this way, similar to other staged separation processes, a plurality of individual filtration steps may be used to achieve a selected purity of filtride. By using pressure to control introduction and electric potential to control filtration, the introduction and filtration steps are decoupled and the device may be used in a continuous filtration process.

In some examples, the molecular filter may be part of an automated system that includes a computing device configured to control the introduction phase and the filtration phase. The computing device may include any one or more of a wide range of devices, including processors (e.g., one or more microprocessors, one or more application specific integrated circuits (ASICs), one or more field programmable gate arrays (FPGAs), or the like), one or more servers, one or more desktop computers, one or more notebook (i.e., laptop) computers, one or more cloud computing clusters, or the like. The computing device may control a fluid source fluidically coupled to the at least one purge port and the at least one inlet port to cause a pressure to be selectively applied to the at least one purge port and the at least one inlet port, may control a voltage source to apply a voltage between the at least one inlet port (and, optionally, the at least one purge port) and the at least one filtrate port.

The molecular filter may be referred to as a short-pass filter, since molecules with a smaller size (e.g., smaller DNA chain) are passed through the slits. The molecular filter may be tunable, in that the voltage and the height, width, or cross-sectional area of the slits may be selected to control the size of the molecules that can pass through the slits and retained in the first channel. In this way, the molecular filters described herein may provide an efficient alternative for gel electrophoresis for sample preparation of long chain DNA molecules, and the molecular filter can also be integrated to lab-on-chip devices for next-generation genome technologies. Sample preparation can be performed while reducing macroscale difficulties, such as, samples that require large amounts of DNA and high initial concentrations of DNA, shearing and contamination possibilities during manual handling between steps, and time and/or labor-intensive sample preparation.

The molecular filters described herein may be used in any techniques that include the purification and analysis of DNA. The molecular filters can be used as an assay replacement for gel electrophoresis, be integrated into a total analysis system for DNA, and be used as a pre-filtration step to filter out unwanted DNA lengths in genomic studies such as long-read sequencing, whole-genome mapping, and cell engineering. The molecular filters may also be used to filter other "long strand" type molecules such as ssDNA (aptamers, filtration step for SELEX, CE-SELEX), RNA, proteins, and polymers based on their electrophoretic mobilities.

In addition, utilizing the molecular filters described herein may reduce data noise in the form of signals and errors caused from relatively small chain DNA when analyzing relatively long chain DNA. Without filtration, many post-processing steps are involved to eliminate these noises/errors in results, which has a large computational cost. Hence, the molecular filters described herein may reduce computational cost of subsequent analytical techniques performed on molecules such as DNA filtered using the molecular filters.

FIG. 1 is a conceptual diagram illustrating an example molecular filter device 10, in accordance with some examples of this disclosure. FIG. 1 illustrates how molecular filter device 10 can filter molecules with a short-pass filter by recovering a filtride that includes relatively long chain DNA molecules. Molecular filter device 10 includes a first channel 40 connected to a second channel 50 by a plurality of slits 30. In other examples, rather than including a plurality of slits 30, molecular filter device 10 may include at least one (e.g., one or more) slit. Plurality of slits 30 and first channel 40 define a channel-slit interface 80 for filtration. Plurality of slits 30 provide the ability to control filtration during operation, e.g., by selection of a height, width, or cross-sectional area of respective slits of plurality of slits 30. First channel 40 is fluidically coupled to at least one inlet port 12, at least one purge port 14, and at least one recovery port 16. For example, inlet port 12 may be fluidically connected to a first end 42 of first channel 40 and recovery port 16 may be connected fluidically to a second end 44 of first channel 40, where first end 42 is opposite second end 44. Purge port 14 may be fluidically coupled to an intermediate portion of first channel 40. Second channel 50 is fluidically coupled to first filtrate port 18 and second filtrate port 20. In general, molecular filter device 10 may include at least one filtrate port.

Molecular filter device 10 may include any number of slits 30. For example, molecular filter device 10 may include tens of slits 30. As a particular example, molecular filter device 10 may include 12 relatively long continuous slits 30 with each having a slit height of approximately 90 nm. In some examples, plurality of slits 30 may be positioned symmetrically about a location at which purge port 14 fluidically connects to first channel 40, as illustrated by third channel 60 in FIG. 1. The range of slit height depends on the size of molecules to be filtered and can be selected to tune the range of short molecules to be filtered from the sample solution added to at least one input port 12. In general, the slit height may be smaller than the radius of gyration (Rg) of the relatively large molecules (filtride) to be retained in first channel 40 and larger than the radius of gyration of the relatively small molecules to be removed from the filtride. For the current example, Rg for lambda DNA (48.5 kilo base pairs; kbp) is about 750 nm and Rg for 2 kbp DNA is about 90 nm.

Channel-slit interface 80 filters the molecules in a sample introduced to first channel 40 via at least one input port 12. Second channel 50 collects all the relatively small molecules that pass through the plurality of slits 30 during filtration. Molecular filter device 10 employs entropic barriers by controlling the size of the slits of plurality of slits 30 relative to the size of molecules to be filtered. For example, each slit of plurality of slits 30 may define a slit height smaller than the entropic size (e.g., radius of gyration) of the relatively large molecules, such as relatively long chain DNA, from which relatively small molecules, such as relatively short chain DNA, are to be removed. In this way, relatively small molecules, such as relatively short chain DNA, preferentially enters slits of plurality of slits 30 at relatively low electric fields to achieve filtration.

In some examples, channels (including first channel 40, second channel 50, and third channel 60) may be microchannels (i.e., channels with a cross-sectional size on the order of tenths to tens of micrometers) and have a height between about 100 nm and about 10,000 nm. In some examples, plurality of slits 30 may be nanoslits (i.e., slits with a cross-sectional size on the order of single digit nanometers to hundreds of nanometers) and have a height between about 1 nm and about 500 nm, such as between about 50 nm and about 500 nm.

At least one inlet port 12 and at least one purge port 14 are configured to be fluidically coupled to a fluid source 24. At least one inlet port 12, at least one purge port 14, and at least one of filtrate ports 18 and 20 are configured to be electrically coupled to a voltage source 26. Recovery port 16 may also be electrically connected to voltage source 26.

In some examples, fluid source 24 and voltage source 26 may be connected to a controller 22, which is configured to control operation of voltage source 26 and fluid source 24.

Figure 2A:
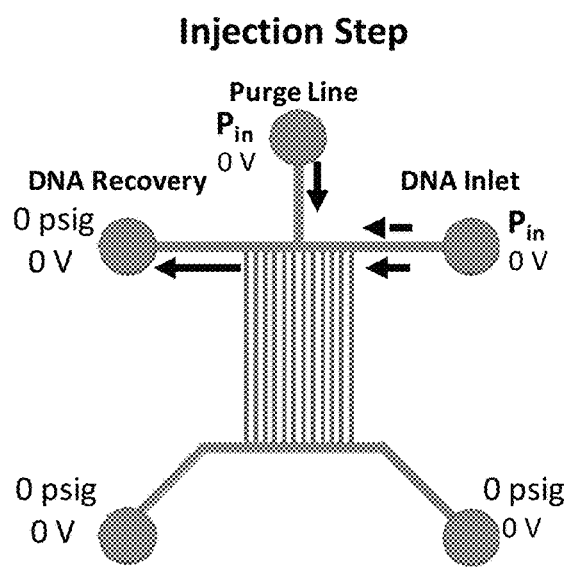
FIGS. 2A and 2B are conceptual diagrams illustrating an example operation of molecular filter devices in an injection phase and a filtration phase, respectively, in accordance with some examples of this disclosure.
Figure 2B:
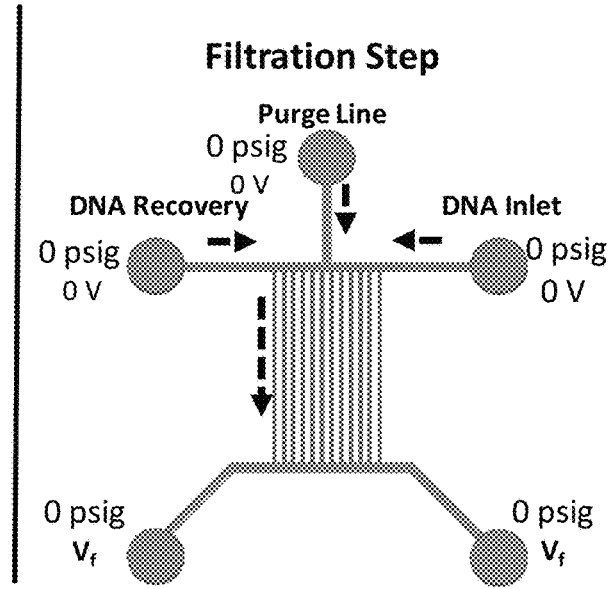

FIGS. 2A and 2B are conceptual diagrams illustrating an example operation of a molecular filter device 10 in an injection step and a filtration step, respectively, in accordance with some examples of this disclosure. During operation of molecular filter device 10, a sample may be introduced to first channel 40 via at least one input port 12 during an introduction phase (also referred to as an injection step). For example, controller 22 may control fluid source 24 to apply a pressure, $P_{in}$, to at least one input port 12 and at least one purge port 14 to push the sample into first channel 40. Fluid source 24 may refrain from applying pressure to recovery port 16 and filtrate ports 18 and 20, as fluid source 24 is not fluidically connected to recovery port 16 and filtrate ports 18 and 20 except through first channel 40, slits 30, and second channel 50. Controller 22 may also control voltage source 26 to refrain from applying a voltage to inlet port 12, at least one purge port 14, recovery port 16, and filtrate ports 18 and 20.

During a filtration phase, as shown in FIG. 2B, controller 22 may be configured to control voltage source 26 to apply a substantially constant voltage between, on the one hand, at least one inlet port 12, at least one purge port 14, and recovery port 16, and, on the other hand, filtrate ports 18 and 20. Controller 22 may also control fluid source 24 to apply a pressure to at least one inlet port 12 and at least one purge port 14 to push filtrate from the sample (e.g., molecules below a threshold size) through plurality of slits 30.

Figure 3A:
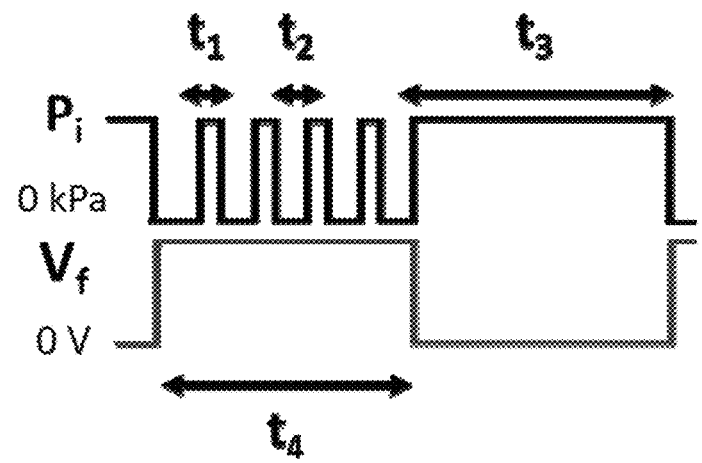
FIGS. 3A and 3B are timing diagrams illustrating example operation of molecular filter devices, in accordance with some examples of this disclosure.
Figure 3B:
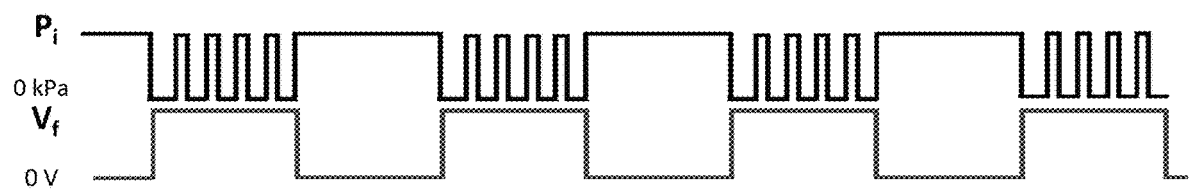

In some examples, controller 22 is configured to cause, during the filtration phase, fluid source 24 to apply an oscillating pressure to at least one inlet port 12 and at least one purge port 14. For example, FIGS. 3A and 3B are timing diagrams illustrating example operation of molecular filter device 10, in accordance with some examples of this disclosure. As shown in FIG. 3A, the introduction phase is represented by duration $t_3$, in which fluid source 24 applies a substantially constant pressure to at least one inlet port 12 and at least one purge port 14 while voltage source 26 refrains from applying voltage to molecular filtration device 10. The filtration phase is represented by duration $t_4$, in which fluid source 24 applies an oscillating pressure to at least one inlet port 12 and at least one purge port 14 and voltage source 26 applies a substantially constant voltage between, on the one hand, at least one inlet port 12, at least one purge port 14, and recovery port 16, and, on the other hand, filtrate ports 18 and 20. The respective time durations, $t_1$ (duration of high pressure periods during the filtration phase), $t_2$ (duration of low pressure periods during the filtration phase), $t_3$ (duration of the introduction phase), and $t_4$ (duration of the filtration phase) may be selected to achieve a selected purification percentage of the filtride (relatively large molecules). As shown in FIG. 3B, in some examples, controller 22 may cause the introduction phase and the filtration phase to be repeated in an alternating pattern.

The combination of constant voltage and oscillating pressure during the filtration phase causes filtride of the sample to concentrate at one or more portions of channel-slit interface 80 between first channel 40 and plurality of slits 30. The filtride may include relatively large molecules (e.g., long chain DNA), and the filtrate may include relatively small molecules (e.g., short chain DNA). Device 10 facilitates removal of relatively small molecules (e.g., short chain DNA fragments) and recovery of relatively large molecules (e.g., long chain DNA molecules) from a molecular mixture (e.g., DNA mixture), which can then be used for downstream genomic applications.

Controller 22 may include, for example, a desktop computer, a laptop computer, a workstation, a server, a mainframe, a cloud computing system, or the like. Controller 22 is configured to control operation of fluid source 24 and voltage source 26. Controller 22 may be communicatively coupled to fluid source 24, voltage source 26, or both using respective communication connections. In some examples, the communication connections may include network links, such as Ethernet, ATM, or other network connections. Such connections may be wireless and/or wired connections. In other examples, the communication connections may include other types of device connections, such as USB, IEEE 1394, or the like. In some examples, controller 22 may include control circuitry, such as one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Figure 4:
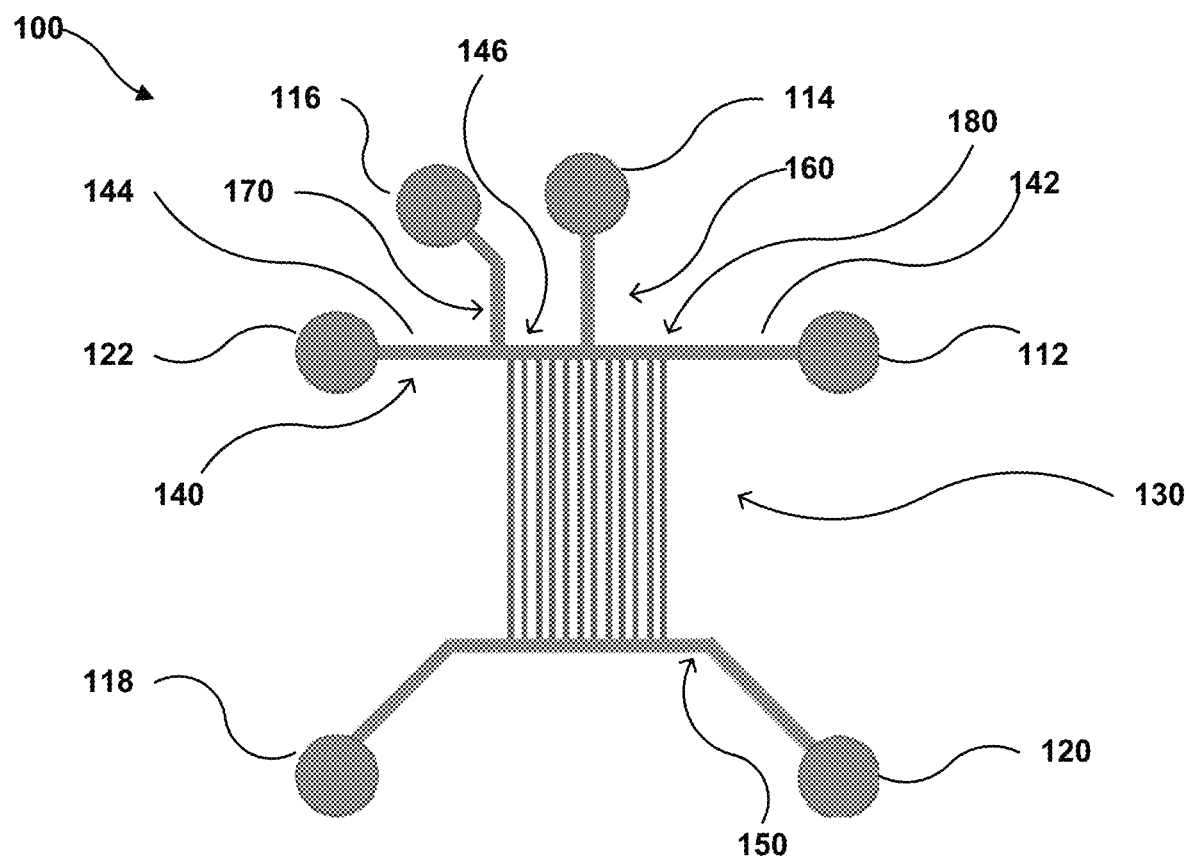
FIG. 4 is a conceptual diagram illustrating another example molecular filter device, in accordance with some examples of this disclosure.

FIG. 4 is a conceptual diagram illustrating another example molecular filter device 100, in accordance with some examples of this disclosure. Molecular filter device 100 may be similar to or substantially the same as molecular filter device 10, aside from the differences described herein. For example, like molecular filter device 10, molecular filter device 100 includes a first channel 140, a second channel 150, a plurality of slits 130, filtrate ports 118 and 120, an input port 112 fluidically coupled to a first end 142 of first channel 140, and a first purge port 114 fluidically coupled by a channel 160 to an intermediate portion of first channel 140. Unlike device 10, device 100 includes a second purge port 122 fluidically coupled to a second end 144 of first channel and a separate recovery port 116 fluidically coupled to first channel 140 by a recovery channel 170. Inclusion of recovery channel 170 may allow for semi-continuous recovery of filtride during the filtration technique by decoupling the filtration and injection cycles.

As shown in FIG. 4, channel 170 fluidically connects first channel 140 to recovery port 116 and is positioned between first purge port 114 and second purge port 122. Channel 170 decouples the injection and filtration at the outlets. The potential at recovery channel 170 may be left floating (e.g., not driven to a selected voltage), which may substantially prevent backflow of filtride in recovery port 116 during filtration.

The operation protocol for molecular filter device 100 will now be described. Due to the location of channel 160 and first purge port 114, molecular filter device 100 separates the two side of first purge port 114 (the central purge line) into pre-filter and main-filter regions 180 and 146, respectively. The pre-filter region 180 is disposed towards inlet port 112 (the molecule inlet side) while the main-filter region 146 is disposed on the recovery port 116 side of first purge port 114. Although not shown in FIG. 4, molecular filter device 100 may be connected to a fluid source 24 and a voltage source 26, which may be controlled by a controller 22, like molecular filter device 10 of FIG. 1.

Figures 5A, 5B:
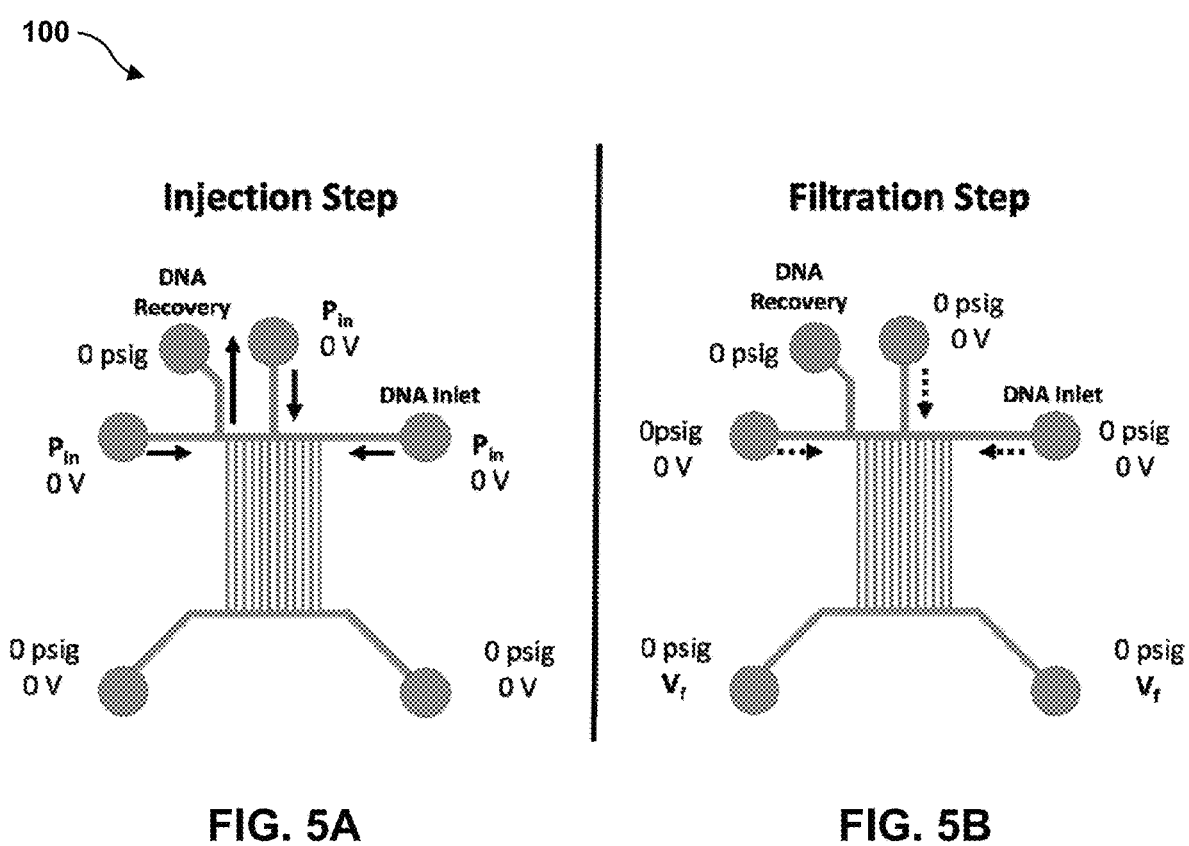
FIGS. 5A and 5B are conceptual diagrams illustrating an example operation of molecular filter devices in an injection phase and a filtration phase, respectively, in accordance with some examples of this disclosure.

FIGS. 5A and 5B are conceptual diagrams illustrating an example operation of molecular filter device 100 in an injection step and a filtration step, respectively, in accordance with some examples of this disclosure. During operation of molecular filter device 100, a sample may be introduced to first channel 140 via at least one input port 112 during an introduction phase (also referred to as an injection step). For example, a controller may control a fluid source to apply a pressure, $P_{in}$, to at least one input port 112, first purge port 114, and second purge port 122 to push the sample into first channel 140. The pressure may not be applied to the recovery port 116 and filtrate ports 118 and 120. The controller may also control the voltage source to refrain from applying a voltage to inlet port 112, purge ports 114 and 122, recovery port 116, and filtrate ports 118 and 120. Since all ports have no voltage applied, no electric field will drive molecules into plurality of slits 130.

During the introduction phase, the concentrated filtride from the pre-filter region 180 moves to the main-filter region 146 and the fresh sample is loaded into the pre-filter region 180 of first channel 140 via fluid pressure applied on inlet port 112. Pressure applied on first purge port 114 and second purge port 122 directs filtride from the main-filter region 146 to recovery port 116.

During a filtration phase, as shown in FIG. 5B, the controller may be configured to control the voltage source to apply a substantially constant voltage between, on the one hand, at least one inlet port 112 and purge ports 114 and 122, and, on the other hand, filtrate ports 118 and 120. The controller may also control the pressure source to apply a pressure to at least one inlet port 112 and purge ports 114 and 122 to push filtrate from the sample (e.g., molecules below a threshold size) through plurality of slits 130. Pressure may not be applied to recovery port 116. Sample continues to be injected in the pre-filter region 180 during the filtration phase due to the pressure applied to input port 112, while the main-filter region 146 further removes the relatively small molecules entered from the pre-filter region 180 during the injection cycle. The automatic change between injection and filtration phases by a controller to control the fluid pressure and applied voltage helps molecular filter device 100 continuously filter.

During the filtration cycle, DNA are filtered depending upon the electric field in plurality of slits 130. The electric field in plurality of slits 130 is controlled by the electric voltage applied at the ports 112, 114, 118, 120, and 122. The dimensions of channels 140, 150, 160, and 170 will also affect the potential drop in the channel and therefore the electric field in plurality of slits 130 fluidically connecting first channel 140 and second channel 150. This implies that electric potential can be changed on ports 112, 114, 118, 120, and 122 by modifying the channel dimensions as long as the same electric field is maintained in plurality of slits 130. The resistor model described with reference to FIGS. 7A and 7B aids in predicting the correct electric potential drops for different channel dimensions 140, 150, 160, and 170.

In some examples, the controller is configured to cause the pressure source to apply an oscillating pressure to at least one inlet port 112 and purge ports 114 and 122 during the filtration phase. As described above with respect to FIGS. 2A and 2B, this may facilitate filtration and concentration of filtride at different positions on channel-slit interface 180 between first channel 140 and plurality of slits 130.

Figure 6:
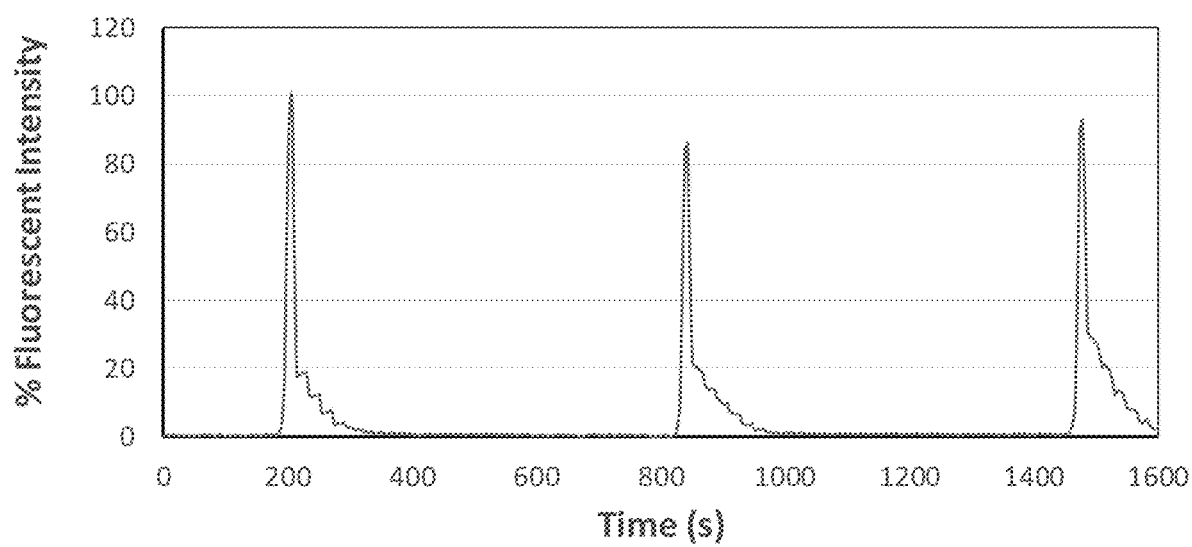
FIG. 6 is a plot illustrating percent fluorescent intensity versus time for recovered DNA from an example molecular filter device, in accordance with some examples of this disclosure.

FIG. 6 is a plot illustrating percent fluorescent intensity versus time measured at recovery channel 170 connected to recovery port 116, for recovered DNA from molecular filter device 100, in accordance with some examples of this disclosure. FIG. 6 demonstrates the pulse-like recovery of filtride (e.g., relatively large molecules) after filtration for molecular filter device 100. Filtride is recovered from recovery port 116 via recovery channel 170 during the filtration cycle. Because recovery port 116 does not have any electric potential, no DNA will be pulled back from recovery channel 170 to the filtration region in first channel 140. This will provide a pulse-like recovery of filtered DNA.

One parameter used to control the filtration process is applied electric voltage (e.g., between, on the one hand, input port 112, first purge port 114, and second purge port 122, and, on the other hand, filtrate ports 118 and 120). The entropic barrier for relatively large molecules (e.g., long chain DNA) decreases with the increase in the electric potential drop across plurality of slits 130. This causes a trade-off between the selectivity of relatively large molecules (e.g., long chain DNA) over relatively small molecules (e.g., short chain DNA) and recovery of the relatively large molecules (e.g., long chain DNA) after filtration. The understanding of the electric voltage at each slit-channel interface 180 for plurality of slits 130 in first channel 140, as well as, second channel 150, may help explain the filtration process in molecular filter device 100 and to design the protocol for the efficient device operation, to achieve efficient filtration.

Figure 7B:
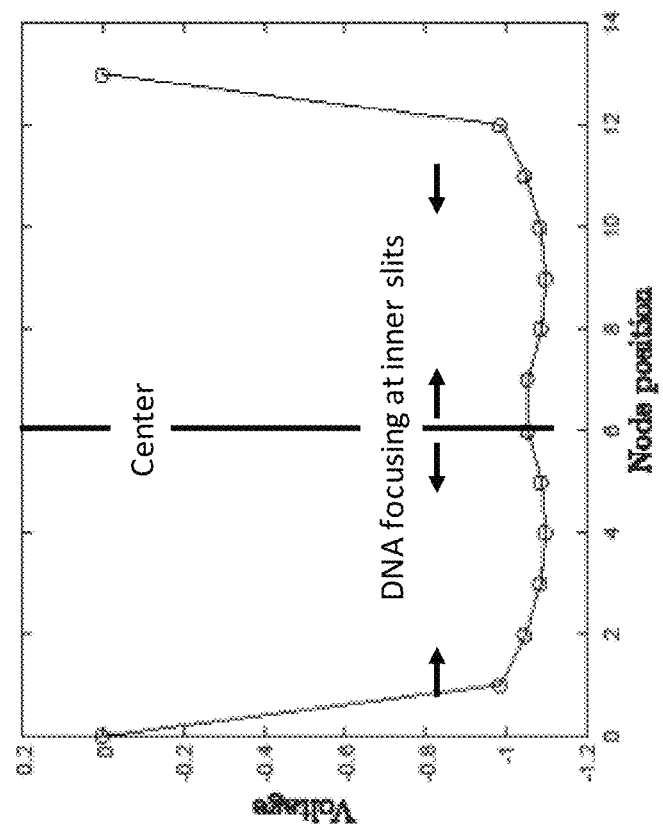
FIGS. 7A and 7B are plots of voltage versus node position for example resistor models representing electric potential as a function of channel-slit interface for an example molecular filter device, in accordance with some examples of this disclosure.
Figure 7A:
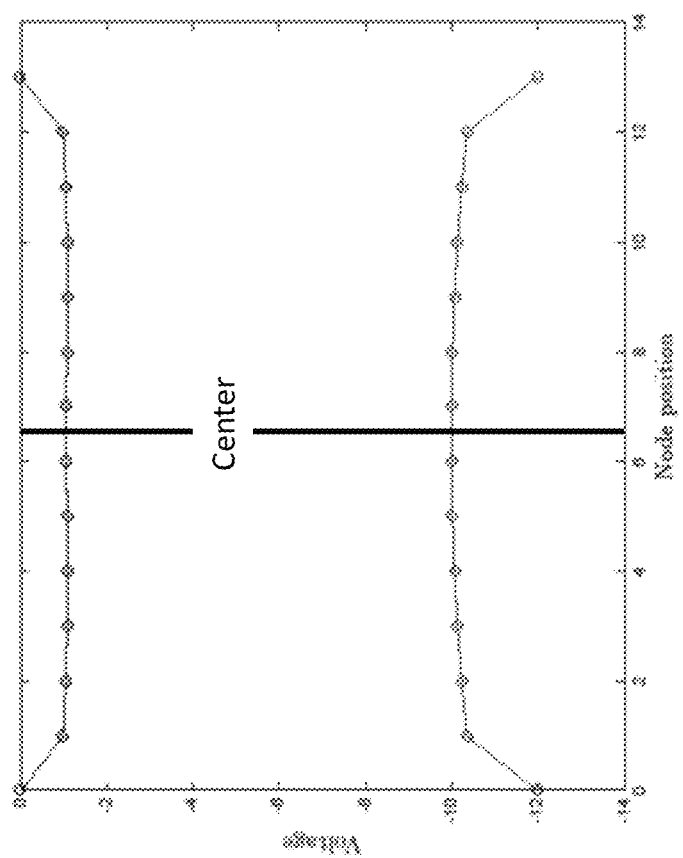

FIGS. 7A and 7B are plots of voltage versus node position for example resistor models representing electric potential as a function of channel-slit interface (node positions within the resistor model) for the plurality of slits 130 in the first channel 140 as well as the second channel 150 for an example molecular filter device 100, in accordance with some examples of this disclosure.

Ports 112, 114, 116, 118, 120, and 122 and interfaces between respective slits of plurality of slits 130 were treated as nodes, and channels 140 and 150 between the nodes were treated as resistors, which depend on dimensions of the respective channels 140 and 150 ($R_r=\rho l/h \times w$; l, h & w), where l, h, and w are the length, width, and height of the respective channel. The depth of first and second channels 140 and 150 were assumed to be 1 micrometer, the depth of slits 130 was assumed to be 100 nanometers, and the length of device 100 was assumed to be 1 cm. First and second purge ports 114 and 122 and input port 112 were kept at ground, while the filtrate ports 118 and 120 were given a fixed potential $V_f$. As the DNA is a negatively charged molecule, the DNA moves opposite to the electric field direction, i.e. towards the higher potential. The electric potential at each node was calculated by applying Kirchhoff's law at each node and Ohm's law in each channel and solving simultaneous equations using Matlab. Assuming the same geometry aside from recovery port 116, the electric potential distribution in both molecular filter devices 10 and 100 were the same because the electric potentials are applied at the same positions and recovery port 116 in molecular filter device 100 is kept floating and does not contribute in the electric potential calculation.

The result of the resistor model showed that the electric potential profiles in first channel 140 and second channel 150 were substantially symmetric across purge channel 160, as shown in FIG. 7A (where the top curve is for first channel 140 and the bottom curve is for second channel 150). As shown in FIG. 7B, there were local minima for the electric potential on either side of first purge port 114. These local minima are the cumulative effect of the potential drops across first channel 140 (which is serpentine) connecting the parallel slits 130. These minima lead to DNA accumulation because they correspond to electric potential minima for the negatively charged DNA. These concentration points arise from the current of ions from first and second purge ports 114 and 122 and input port 112 towards filtrate ports 118 and 120 via the plurality of slits 130. The plurality of slits 130 are connected in parallel between the first and second channels 140 and 150, so the ionic current is distributed between the plurality of slits 130, leading to a non-uniform electric potential within first and second channels 140 and 150. This suggested that the electrical potential minimum will be the filtride focusing location where the majority of filtration takes place on either side of first purge port 114. This was later verified through experiments. The resistor model shown in FIGS. 7A and 7B is applicable to both examples, device 10 and device 100.

Figure 8:
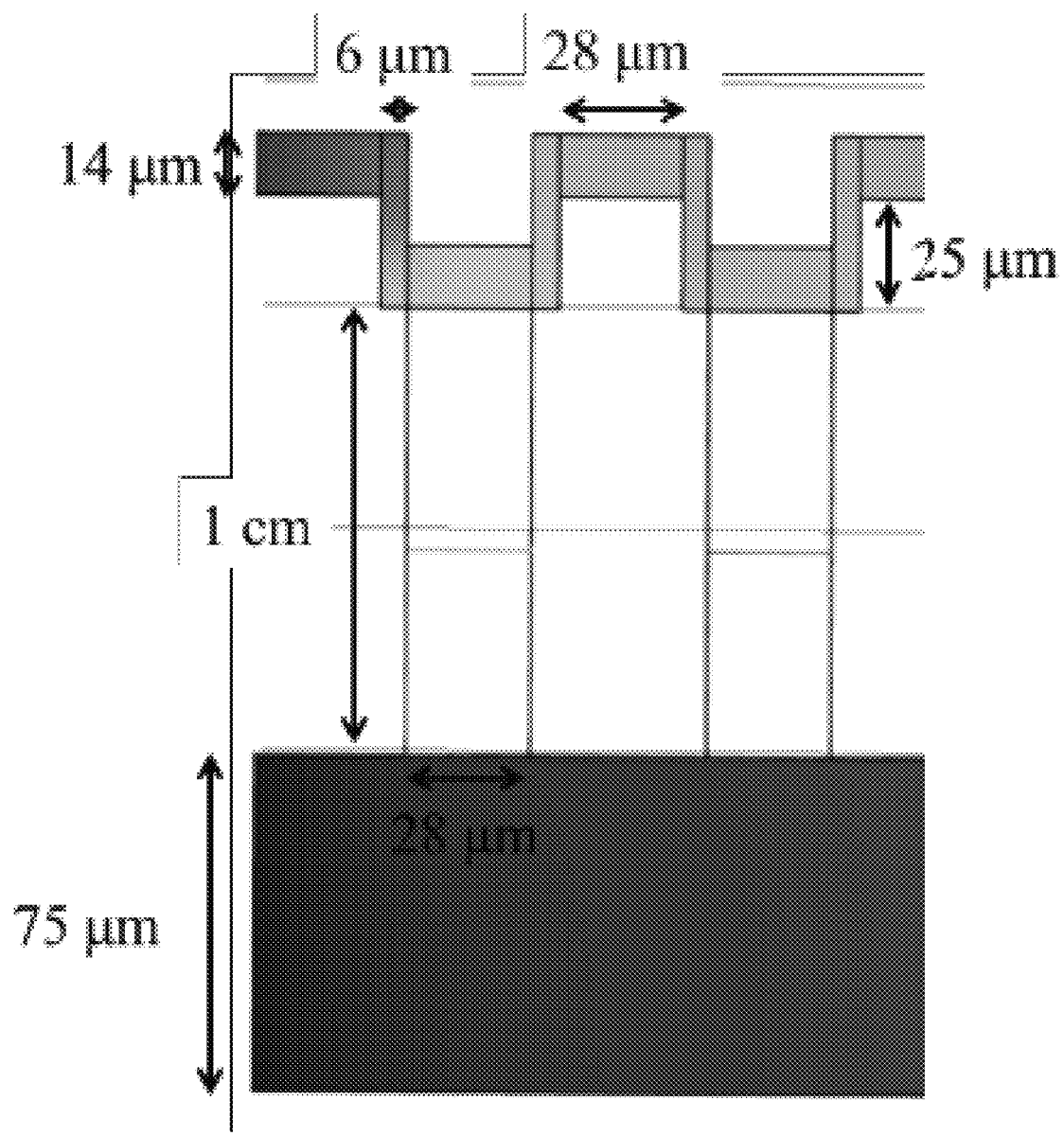
FIG. 8 is a conceptual diagram illustrating the parameters used for a COMSOL model of an example molecular filter device.

A 3D COMSOL model of the device predicted similar potential drops and two focusing zones in the device, indicating that the simple resistor model is a good approximation of the actual device geometry. FIG. 8 is a conceptual diagram illustrating the parameters used for a COMSOL model of an example molecular filter device 100. The model includes a serpentine first channel 140 with a depth of 1 micrometer, twelve parallel nanoslits with depths of 90 nm, and the other dimensions shown in FIG. 8.

The operation of molecular filter devices 10 and 100 may be understood as the balance between two time scales. The first time scale is the residence time for molecules at the interface between first channel 140 and slits 130. To a first approximation, the residence time is given by the duration of the filtration step $t_4$ in FIG. 3A. This estimate is an upper bound, as the DNA molecules require time to be transported to the interface when the voltage is applied. Moreover, the residence time differs between molecules due to their different initial positions at the start of the filtration step. However, the residence time should be independent of molecular weight to a first approximation, since the free-solution electrophoretic of molecules such as DNA is independent of size (e.g., for DNA molecules larger that 400 base pairs). If anything, a size-dependent mobility, if present, is expected to enhance filtration because it would slow the rate at which larger molecules accumulate at the interface between first channel 140 and slits 130.

The second time scale is the characteristic time for escape over the entropic barrier. The entrapment time of long DNA has been modeled with an equation:

$$\tau = \tau_0 \exp(\alpha/E_S kT)$$

where $\tau_0$ and $\alpha$ are parameters that depend on the size of the molecule, $E_S$ is the electric field strength in slits 130, and kT is the thermal energy. The prefactor $\tau_0$ represents the frequency of attempts to escape an entropic trap. Prior work suggests that $\tau_0$ is inversely proportional to the size of the DNA molecule because larger molecules present a larger cross-section at the interface, and thus have more opportunities to insert a hairpin into one of slits 130. The above equation has been applied to model long DNA, and it is likely to overestimate a trapping time for short DNA. The other parameter, $\alpha$, is related to the free energy barrier for moving the molecule form the weak confinement of first channel 140 to the strong confinement of one of slits 130 in the tilted potential energy landscape provided by the applied electric field. Simulation work suggests that $\alpha$ depends on the molecular weight of the DNA at low and moderate electric fields; larger DNA experience a higher entropic penalty due to the reduction in conformational phase space upon entry into the slit. At higher electric fields, $\alpha$ becomes independent of molecular weight for large DNA because its magnitude is governed by the entropic cost for inserting a "beachhead" of DNA into one of slits 130; the strong electric field then sucks the rest of the DNA into the one of slits 130. If the entire size of the DNA is smaller than this beachhead, then $\alpha$ should remain a function of molecular weight for all electric field strengths.

A remarkable feature of entropic trapping as a size-based separation is that the longer DNA elute first from the device under relatively high electric fields because the dependence of $\tau$ on $\tau_0$ is more important that the dependence on $\alpha$. However, at sufficiently low electric fields, as used in molecular filter devices 10 and 100, the parameter $\alpha$ becomes more important than $\tau_0$ in governing the escape time because it appears in the exponential.

The filtration performance of molecular filter devices 10 and 100 may be tuned by considering the ratio of the two relevant time scales:

$$\beta = t_4/\tau$$

for a given DNA size. If $\beta \gg 1$, then that size molecule should escape through the entropic trap and be filtered out. Conversely, if $\beta \ll 1$, then most of the molecules with that size should be retained in the microchannel and eventually shuttled to recovery port 116 during the subsequent injection step. However, the intrinsic physics embodied by the equation for τ imply that a single entropic trap will not provide an infinite selectivity since β is always finite and non-zero. Moreover, it is worth noting that β represents the characteristic time for the distribution of trapping times; even for β<<1, some of the molecules will still escape.

Figure 9:
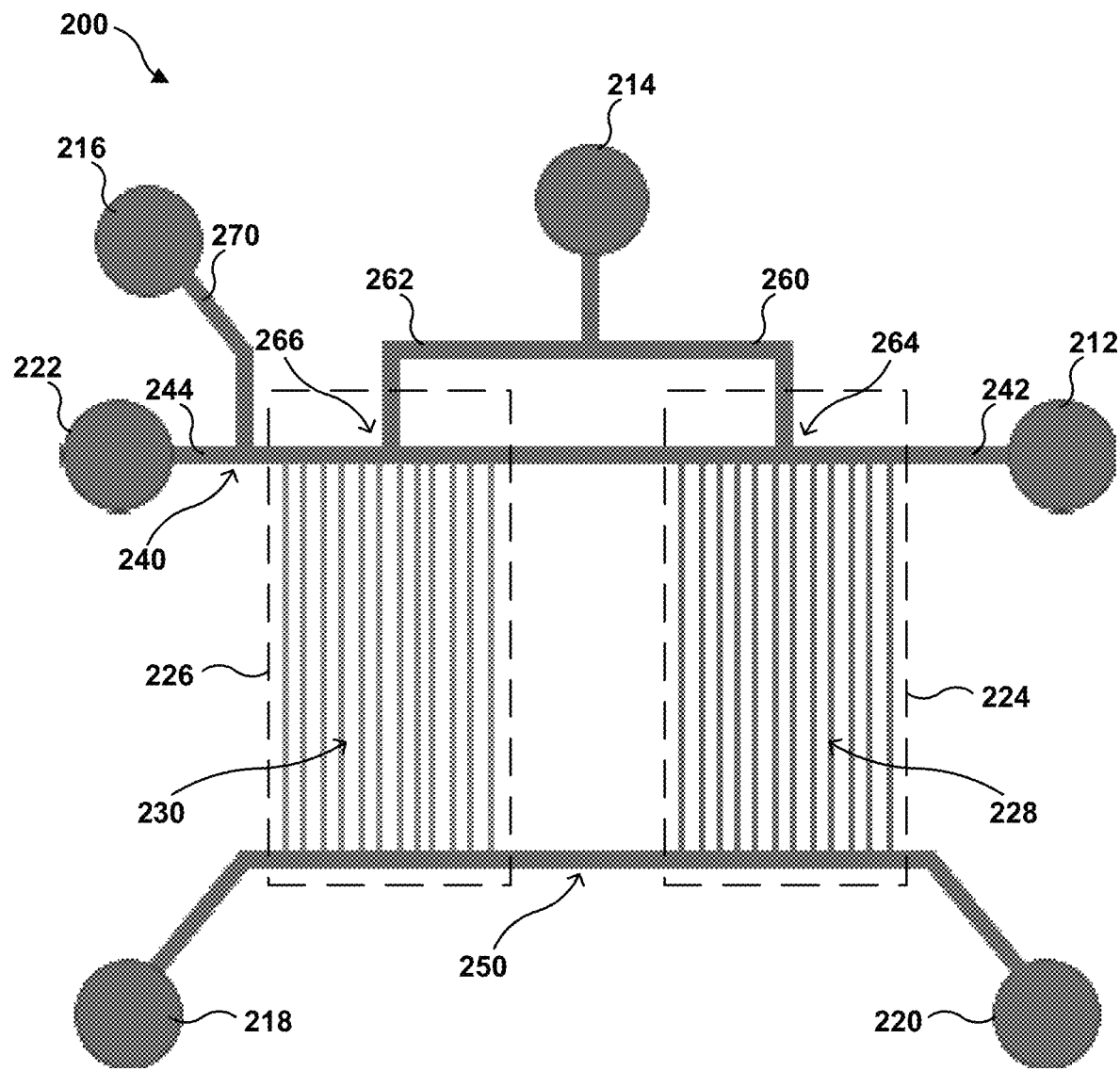
FIG. 9 is a conceptual diagram illustrating another example molecular filter device including two stages in series, in accordance with some examples of this disclosure.

FIG. 9 is a conceptual diagram illustrating another example molecular filter device 200, in accordance with some examples of this disclosure. Molecular filter device 200 may be similar to or substantially the same as molecular filter device 100 of FIG. 4, aside from the differences described herein. For example, like molecular filter device 100, molecular filter device 200 includes a first channel 240, a second channel 250, filtrate ports 218 and 220, an input port 212 fluidically coupled to a first end 242 of first channel 240, and a first purge port 214 fluidically coupled by a first purge channel 260 and a second purge channel 262, respectively, to a first intermediate portion 264 and a second intermediate portion 266 of first channel 240. Device 200 also includes a second purge port 222 fluidically coupled to a second end 244 of first channel and a separate recovery port 216 fluidically coupled to first channel 240 by a recovery channel 270. Inclusion of recovery channel 270 may allow for semi-continuous recovery of filtride during the filtration technique by decoupling the filtration and injection cycles.

Unlike device 100, device 200 includes a first stage 224 and a second stage 226. First stage 224 includes a first at least one slit (e.g., first plurality of slits 228) and second stage 226 includes a second at least one slit (e.g., first plurality of slits 230). First stage 224 is upstream of second stage 226 along first channel 240 (conversely, second stage 226 is downstream of first stage 224 along first channel 240). Recovery port 216 and recovery channel 270 connect to first channel 240 downstream of second stage 226. Inlet port 212 connects to first channel 240 upstream of first stage 224.

First purge channel 260 may fluidically connect to first channel 240 at or near a midpoint of first stage 224 (e.g., such that half of first plurality of slits 228 connect to first channel 240 upstream of first purge channel 260 and half of first plurality of slits 228 connect to first channel 240 downstream of first purge channel 260). Similarly, second purge channel 262 may fluidically connect to first channel 240 at or near a midpoint of second stage 226 (e.g., such that half of second plurality of slits 230 connect to first channel 240 upstream of second purge channel 262 and half of second plurality of slits 230 connect to first channel 240 downstream of second purge channel 262). In this way, each of first stage 224 and second stage 226 may operate similarly to molecular filter device 100 of FIG. 4, aside from filtride from first stage 224 proceeding to second stage 226 instead of a recovery port. Filtride form second stage 226 proceeds to recovery port 216.

The configuration shown in FIG. 9 may be extended to any number of stages, with an inlet port 212 upstream of the first stage, purge channels connected to first channel 240 at each stage, and a recovery port 216 and second purge port 222 downstream of the final stage.

Figure 10A:
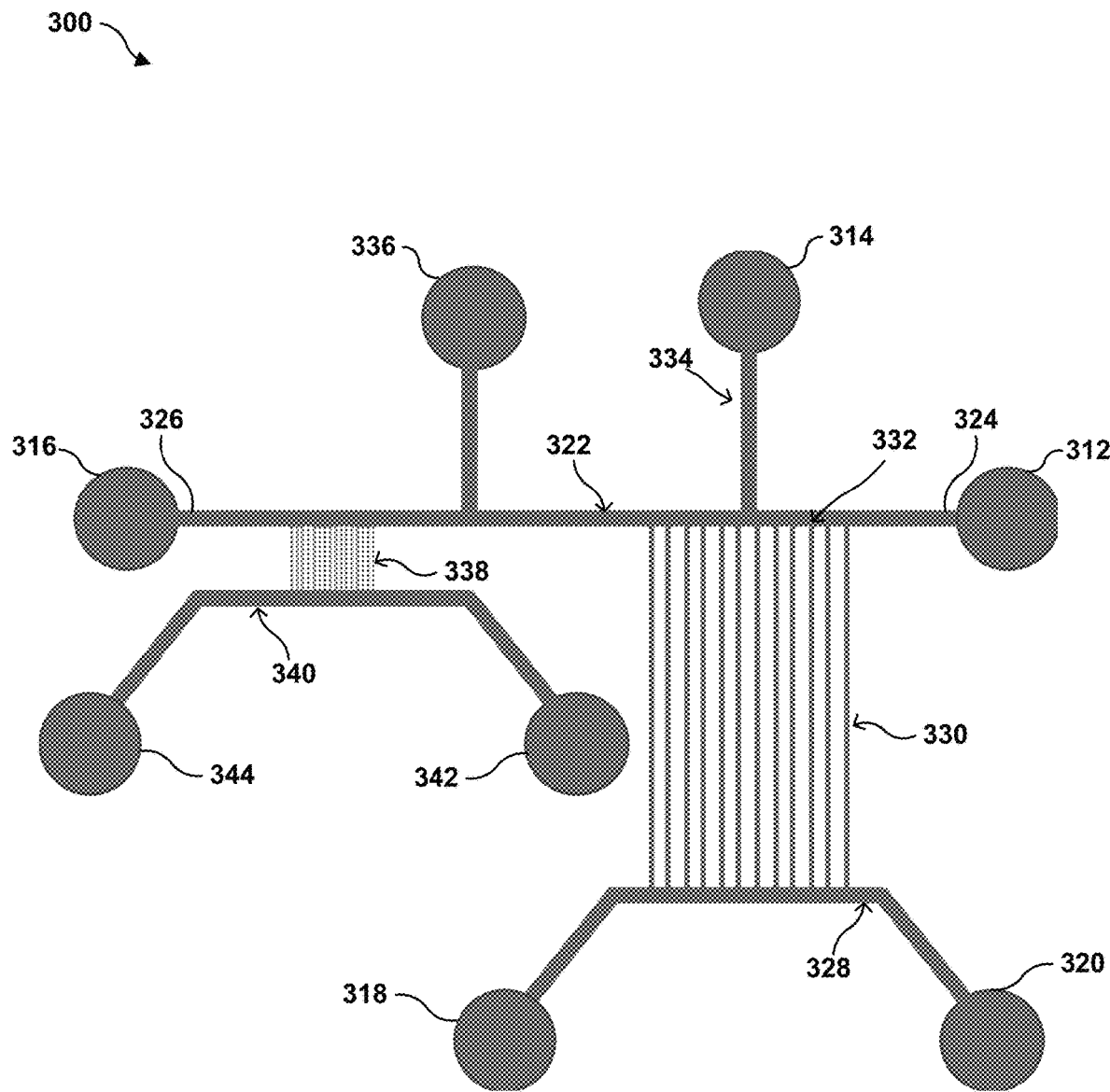
FIG. 10A is a conceptual diagram illustrating another example device including a molecular filter device integrated with a genome mapping nanochannel device, in accordance with some examples of this disclosure.
Figure 10C:
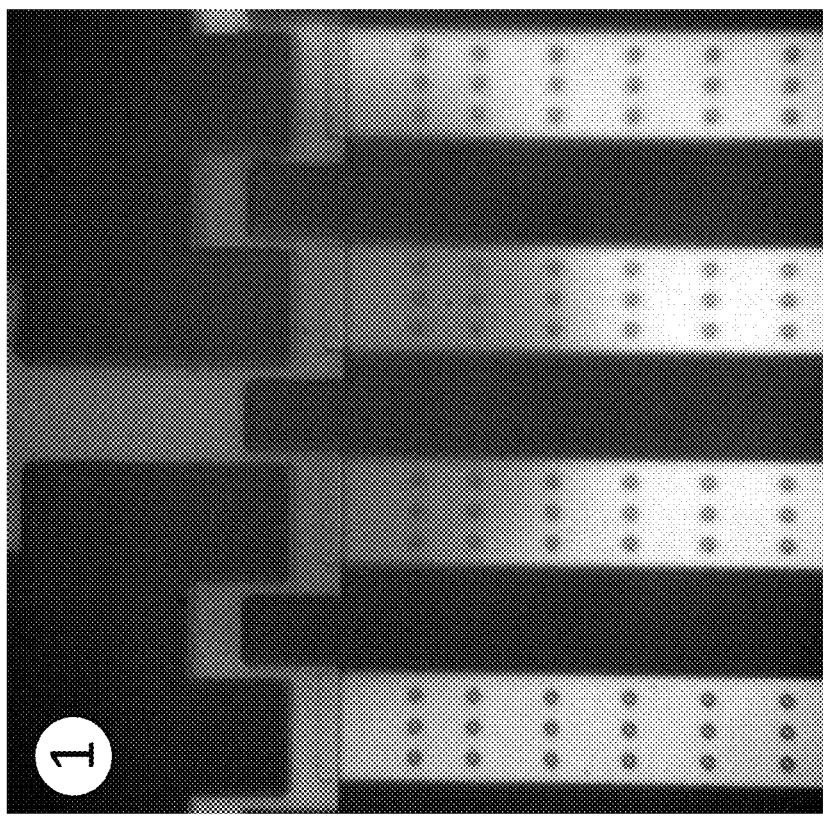
FIGS. 10B and 10C are micrographs of the example molecular filter device and genome mapping nanochannel device of FIG. 10A.
Figure 10B:
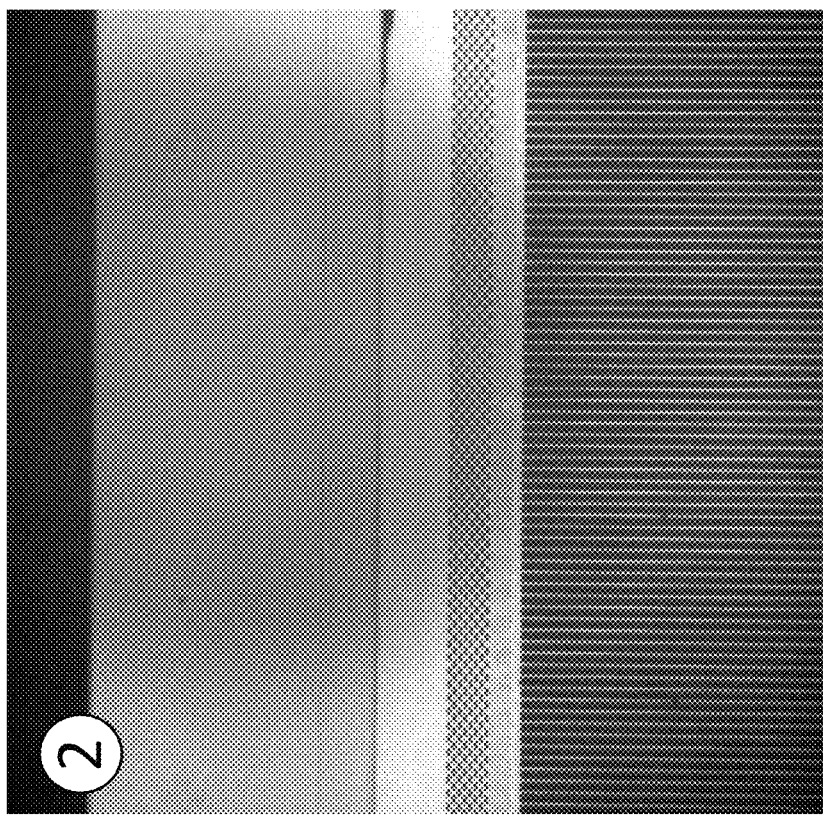

In some examples, a molecular filter device may be incorporated in a lab on a chip with another device, such as a genomic nanochannel device. FIG. 10A is a conceptual diagram another example device 300 including a molecular filter device 302 integrated with a genome mapping nanochannel device 304, in accordance with some examples of this disclosure. FIG. 10B is a micrograph of the molecular filter device 302 of device 300 and FIG. 10C is a micrograph of the genome mapping nanochannel device 304 of device 300. Device 300 includes a first channel 322 connected to a second channel 328 by a plurality of slits 330. In other examples, rather than including a plurality of slits 330, molecular filter device 300 may include at least one (e.g., one or more) slit. Plurality of slits 330 and first channel 322 define a channel-slit interface 332 for filtration. Plurality of slits 330 provide the ability to control filtration during operation, e.g., by selection of a height, width, or cross-sectional area of respective slits of plurality of slits 330. First channel 322 is fluidically coupled to at least one inlet port 312, a first purge port 314, a second purge port 336, and at least one recovery port 316. For example, inlet port 312 may be fluidically connected to a first end 324 of first channel 322 and recovery port 316 may be connected fluidically to a second end 326 of first channel 322, where first end 324 is opposite second end 326. First purge port 314 may be fluidically coupled to an intermediate portion of first channel 322, e.g., near a midpoint of channel-slit interface 332. Second channel 328 is fluidically coupled to first filtrate port 318 and second filtrate port 320. In general, molecular filter device 300 may include at least one filtrate port. Molecular filter device 302 of device 300 may operate substantially similar to any one of molecular filter devices 10, 100, or 200.

Device 300 also includes a genome mapping nanochannel device 304. Genome mapping nanochannel device 304 include a portion of first channel 322 near second end 326, a plurality of nanochannels 338 fluidically connected in parallel between first channel 322 and a third channel 340, and ports 342 and 344 fluidically connected to ends of third channel 340. Second purge port 336 may be fluidically connected to a fluid port through which fluid may be introduced to first channel 322 to, along with fluid from first purge port 314, urge filtride from the portion of first channel 322 near channel-slit interface 332 to a portion of first channel 322 near plurality of nanochannels 338. The operation of genome mapping nanochannel device 304 is described in a article titled "Experimental Evidence of Weak Excluded Volume Effects for Nanochannel Confined DNA," by Gupta et al. in *ACS Macro Lett.* 2015, 4, 759-763, the entire content of which is incorporated herein by reference.

Molecular filter devices 10, 100, and 200 may be formed using any suitable technique in any suitable substrate material. For ease of explanation, the remainder of the description will focus on molecular filter device 100, although the description is equally applicable to molecular filter devices 10 and 200. For example, molecular filter device 100 may be formed from a semiconductor material, such as silicon, germanium, silicon carbide, gallium nitride, gallium arsenide, or the like; fused silica or another glass; a polymer; or the like. Similarly, any suitable technique for defining channels and slits in a substrate may be used to form molecular filter device 100, including, for example, lithography.

Figure 11:
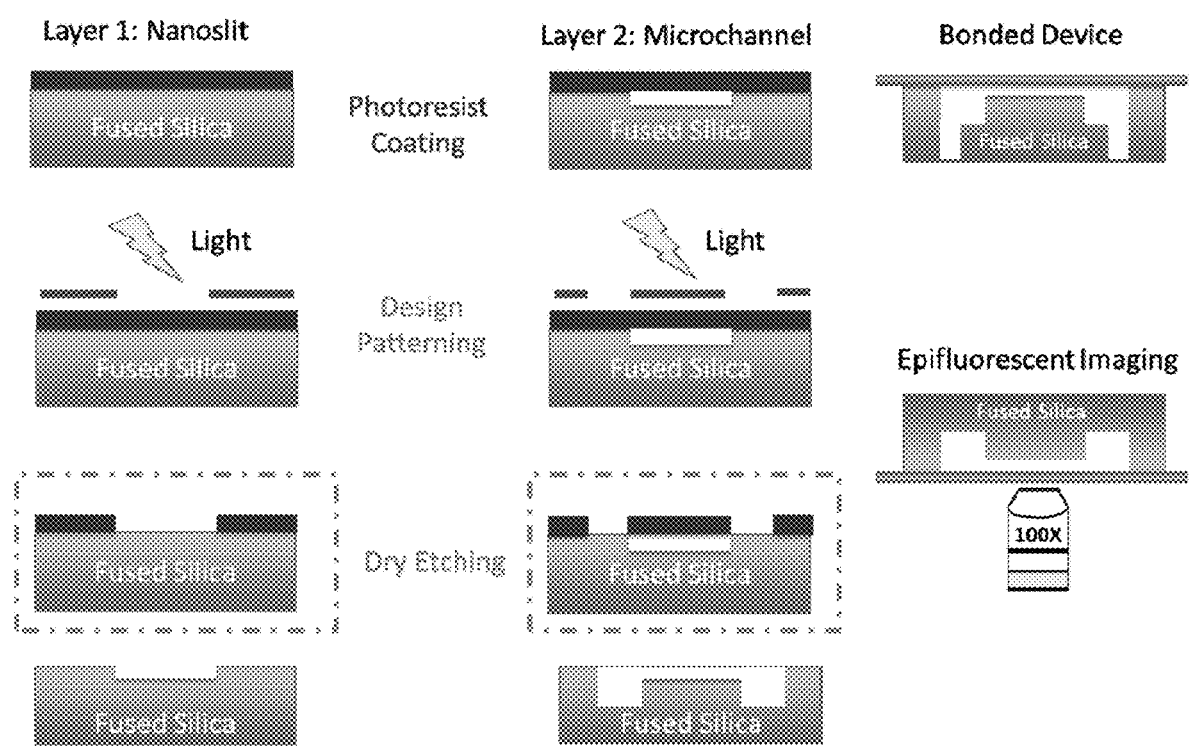
FIG. 11 is a schematic diagram illustrating example steps for fabricating a molecular filter device, in accordance with some examples of this disclosure.

FIG. 11 is a schematic diagram illustrating example steps for fabricating molecular filter device 100, in accordance with some examples of this disclosure. Fused silica was used as the substrate for fabrication as fused silica is an insulating material suitable to apply an electric field for electrophoresis, has good optical properties for epifluorescence microscopy, and has developed protocols to fabricate micro- and nano-scale features. The 2-step fabrication involved sequential fabrication of slits 130 and channels 140, 150, 160, and 170 in a 4" fused silica substrate. Fabrication of both layers involved patterning of the design in a photoresist and then etching the exposed glass surface to desired depth by controlling the etching time. The photoresist acted as a masking layer, which helped in controlling the etching of glass to the selected area. Glass was etched by reactive ion etching (RIE). RIE involved reacting the bare substrate surface with a chemical plasma that chemically reacts with silica to form volatile products, which further exposed a new surface for etching. A different etch duration was used to control the final depth of each features.

Multiple molecular filter devices 100 were fabricated on a single 4" wafer that were then cut-out using a wafer-saw. Through-holes were drilled in ports 112, 114, 116, 118, 120, and 122 using a sandblaster. Finally, molecular filter device 100 was sealed with 170-um thick coverslip through thermal bonding. A fused silica substrate was used to demonstrate the working principle. Similar fabrication can be done in silicon, elastomer, and plastics, which support small scale fabrication as well as ideal for bulk manufacturing.

Although the preceding discussion primarily described using molecular filter devices 10, 100, 200 for separating long chain DNA molecules from short chain DNA molecules, molecular filter devices 10, 100, 200 may be used for separating any molecules based on size. For example, chemistry may be performed to label DNA, RNA, proteins or the like in at least one inlet port 12, 112, or 212 with a fluorescent, magnetic, or other marker. Molecular filter devices 10, 100, 200 then may be used to filter the labelled or marked DNA, RNA, proteins or the like from residual, unreacted marker molecules.

EXAMPLES

The air pressure used for the working examples shown in FIGS. 12-22 was 2.5 kPa. The upper limit of the pressure depends upon the hydraulic resistance of plurality of slits 30 and 130 so that negligible pressure-driven flow takes place in plurality of slits 30 and 130. The upper limit can be calculated using the Poiseuille flow equation to predict the cut-off pressure that can be applied for injection.

The fluorescent intensity plots in FIGS. 12-22 for molecular filter device 10 involve DNA molecules labeled with fluorophore molecule (YOYO-1) and the intensity profiles were obtained through in-situ epifluorescence microscopy at different locations of the molecular filtration device.

The molecular filter device used to generate the data shown in FIGS. 12-15 included a construction similar to molecular filter device 10 shown in FIG. 1. All slits 30 were about 90 nm high and the channel height was about 900 nm. The molecular filter device 10 included 12 slits in total (six on each side of a central purge port). Each slit was about 0.96 cm long and about 28 µm wide. All channels connecting the ports to the first channel 40 were 75 µm wide. The second channel 50 and all channels connecting the filtration ports 18 and 20 to the second channel 50 were also 75 µm wide. The first channel 40 near the slit-channel interface 80 was 14 µm wide.

Figure 12:
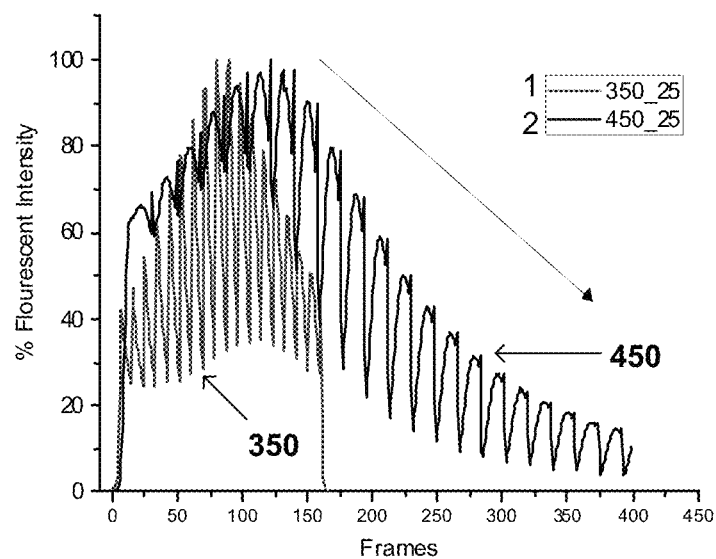
FIG. 12 is a plot illustrating percent fluorescent intensity versus frames for an example molecular filter device, in accordance with some examples of this disclosure.

FIG. 12 is a plot illustrating percent fluorescent intensity versus frames for an example molecular filter device, in accordance with some examples of this disclosure. FIG. 12 illustrates that filtration of short DNA molecules (100 bp ladder) from the first channel increased as DNA spent time on the channel-slit interface 80, increasing from approximately 55% (for $t_4$=350 s) to approximately 80% (for $t_4$=450 s). The injection phase was about 25 s long.

Figure 13:
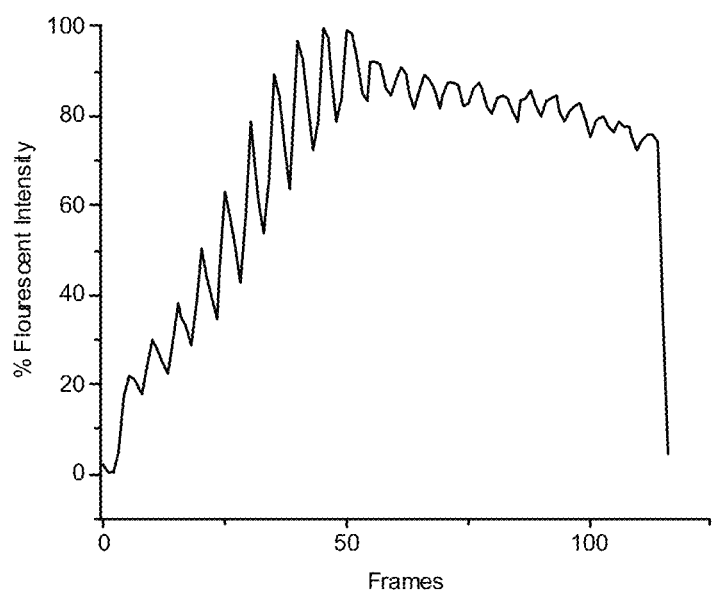
FIG. 13 is a plot illustrating percent fluorescent intensity versus frames for an example molecular filter device, in accordance with some examples of this disclosure.

FIG. 13 is a plot illustrating percent fluorescent intensity versus frames for an example molecular filter device, in accordance with some examples of this disclosure. FIG. 13 displays retention of long chain DNA (lambda DNA) during filtration. The long chain DNA was filtered using 2.5 kPa and 15 V with $t_4$=450 s and $t_3$=25 s, denoted as 450-_25 s in this example.

Figure 14:
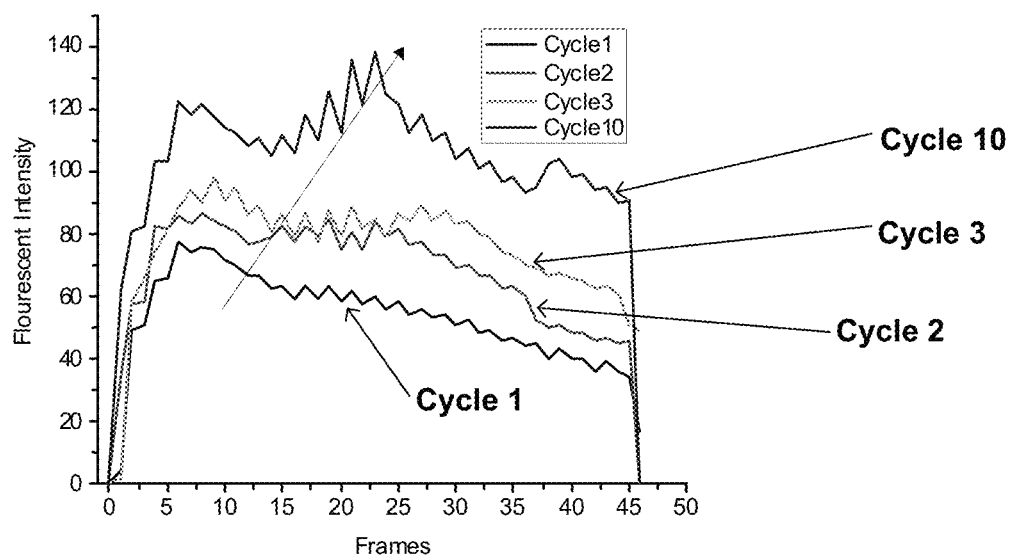
FIG. 14 is a plot illustrating fluorescent intensity versus frames for an example molecular filter device, in accordance with some examples of this disclosure.

FIG. 14 is a plot illustrating fluorescent intensity versus frames for an example molecular filter device, in accordance with some examples of this disclosure. FIG. 14 shows an accumulation of DNA at each filtration cycle, where there is an increase in the fluorescence intensity because of accumulation of unfiltered DNA. Short chain DNA (2 kbp DNA) was filtered using 2.5 kPa and 15 V with $t_4$=450 s and $t_3$=25 s. The accumulation of DNA from the previous cycle shows the limitation of molecular filter device 10.

Figure 15:
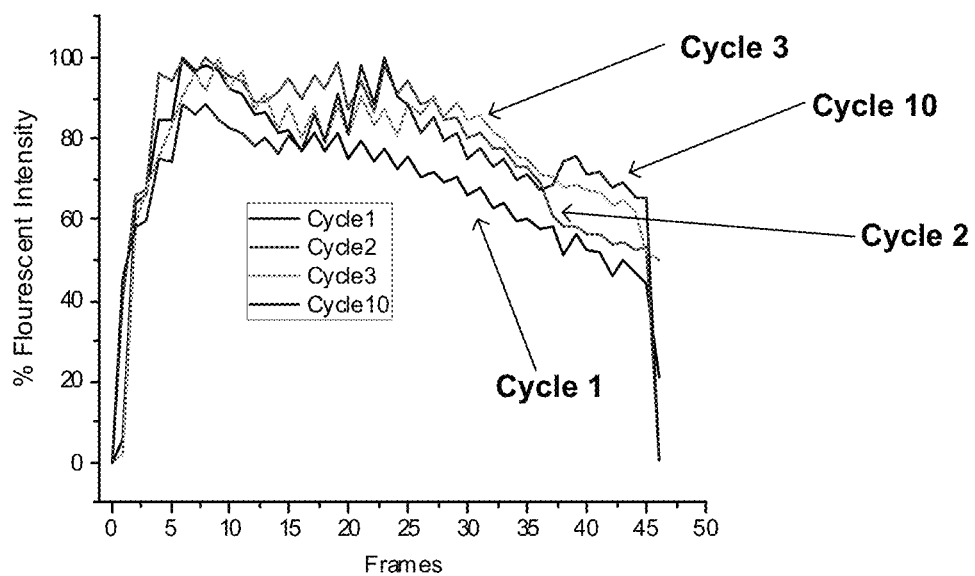
FIG. 15 is a plot illustrating percent fluorescent intensity versus frames for an example molecular filter device, in accordance with some examples of this disclosure.

FIG. 15 is a plot illustrating percent fluorescent intensity versus frames for an example molecular filter device, in accordance with some examples of this disclosure. FIG. 15 shows an accumulation of DNA at each filtration cycle, where there is a reduction in filtration efficiency from approximately 60% to approximately 35%. Short chain DNA (2 kbp DNA) was filtered using 2.5 kPa and 15 V with $t_4$=450 s and $t_3$=25 s. Again, the accumulation of DNA from the previous cycle shows the limitation of molecular filter device 10.

The molecular filter device used to generate the data shown in FIGS. 16A-22 included a construction similar to molecular filter device 100 shown in FIG. 4. All slits 130 were about 90 nm high and the channel height was about 900 nm. The molecular filter device 100 included 12 slits in total (six on each side of a central purge port). Each slit of slits 130 was about 0.96 cm long and about 28 µm wide. All channels connecting the ports 112, 114, and 122 to the first channel 140 were 75 µm wide. The second channel 150 and all channels connecting the filtration ports 118 and 120 to the second channel 150 were also 75 µm wide. The first channel 140 near the slit-channel interface was 14 µm wide.

For FIGS. 16A-22, the operability of device 100 is shown by the proof-of concept results using short chain DNA (2 kbp DNA) and long chain DNA (lambda DNA). The filtration process was quantified through epifluorescent imaging of fluorescently labelled DNA molecules with 100×-oil objective. The results showed a high recovery of long chain DNA as compared to the short chain DNA molecules at same operating condition. The absolute recovery of long chain DNA decreased with the increase in the filtration voltage because of reduction in the entropic barrier with stronger electric field at the channel-slit interface 180 in first channel 160.

Figure 16A:
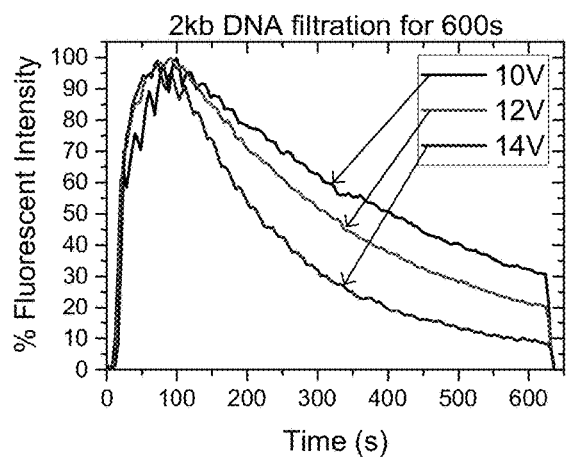
FIGS. 16A and 16B are plots illustrating percent fluorescent intensity versus time as a function of applied voltage for an example molecular filter device at two different DNA lengths, in accordance with some examples of this disclosure.
Figure 16B:
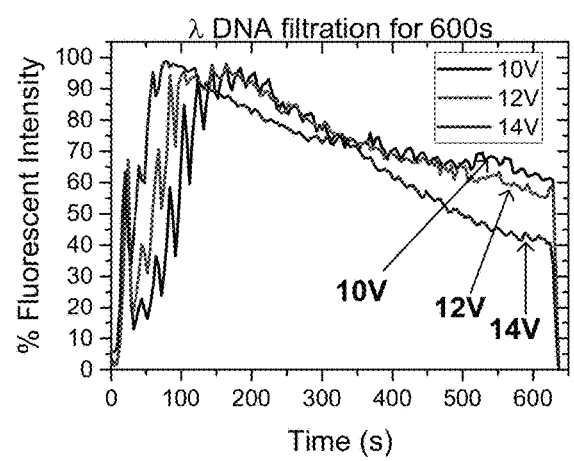

FIGS. 16A and 16B are plots illustrating percent fluorescent intensity versus time as a function of applied voltage for an example molecular filter device using two different DNA lengths, in accordance with some examples of this disclosure. For FIGS. 16A and 16B, both set of experiments were performed separately with DNA labeled YOYO-1. FIGS. 16A and 16B show higher filtration voltage allowed more filtration of short chain DNA but also results in more long chain DNA in the filtrate. Some loss of long chain DNA is also because the long chain was converted to small DNA fragments during DNA loading due to hydrodynamic shear.

The filtration pressure of 2.5 kPa can be further increased as long as there is negligible pressure-driven flow of liquid in the plurality of slits. This can be determined by the Poiseuille flow equation to predict the cut-off pressure that can be applied for injection. Preferably, high pressure is good for fast injection. Oscillation frequency and the duration of injection and filtration cycles are dependent on the filtration voltage and injection pressure. These parameters can be tuned and optimized for each particular set of conditions.

Additional devices were patterned in DOW® S1813 positive photoresist (available from Dow Chemical Company, Midland, Mich.) using optical lithography followed by reactive ion etching using a mixture of Ar/CF$_4$/CHF$_3$ to transfer the patterns into a 4-inch diameter, 0.5 mm thick fused silica substrate (available from UniversityWafer, Inc., South Boston, Mass.). The etch depths for the slits and channels were controlled by controlling the etching duration for each layer to achieve desired depth. The channel depths were quantified using a profilometer (KLA-Tencor P7 Stylus Profiler, from KLA-Tencor, Milpitas, Calif.). Final devices were further characterized using scanning electron microscopy (JEOL 6610, JEOL Ltd., Akishima, Tokyo, Japan). After dicing nine devices with a wafer saw, access holes for the ports were sand blasted. The completed substrate was then RCA-cleaned and thermally bonded to a 170 μm coverslip in a 1000° C. furnace.

Figure 17A:
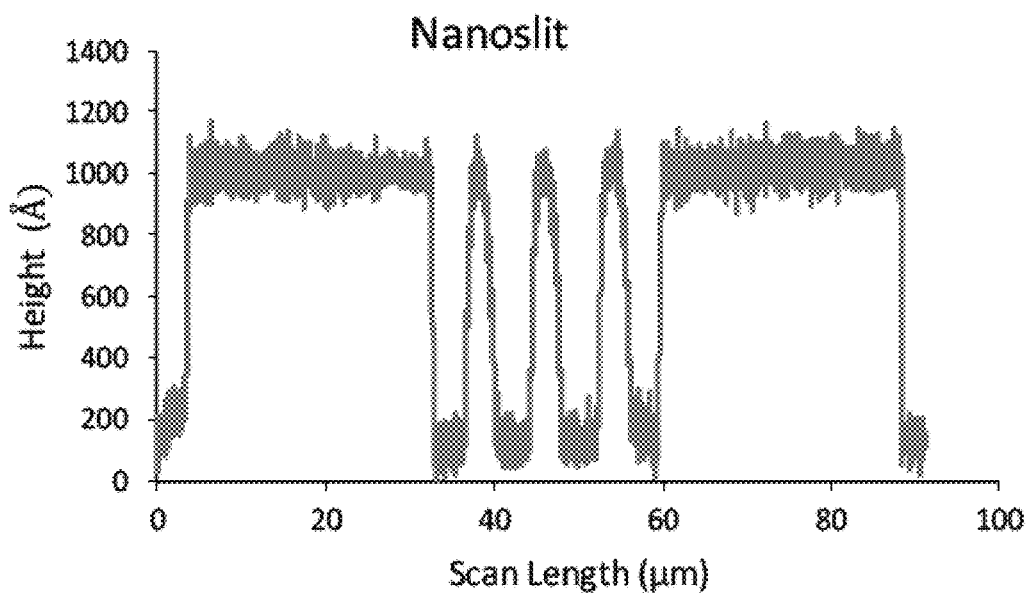
FIG. 17A is a plot showing a profilometer profile of nanoslits for an example molecular filter device.
Figure 17B:
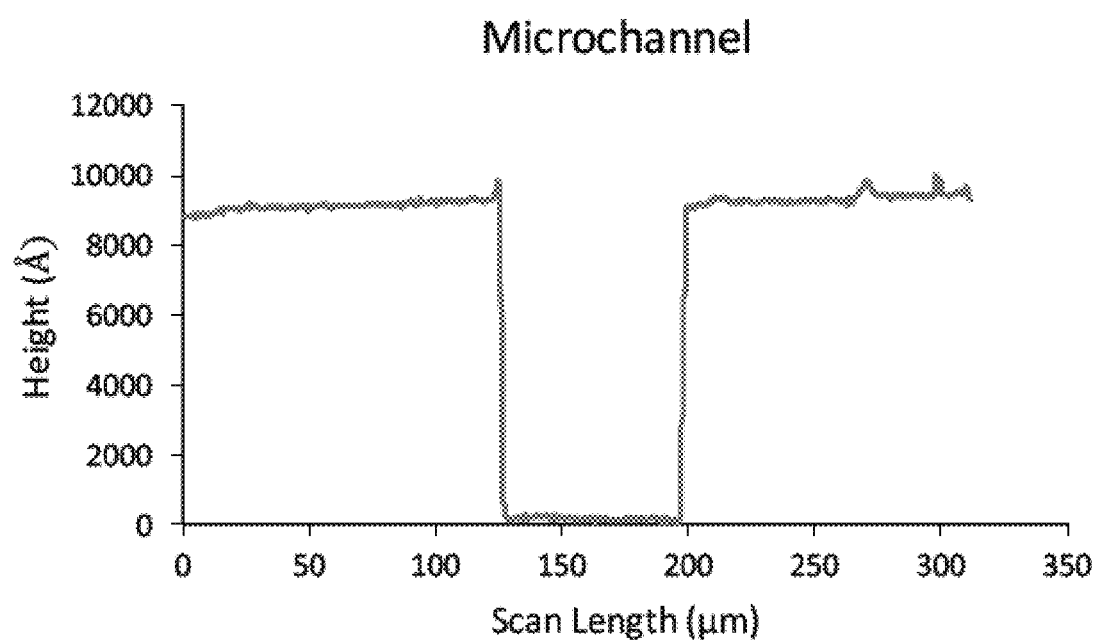
FIG. 17B is a plot showing a profilometer profile of a microchannel for the example molecular filter device of FIG. 17A.

Nine devices were fabricated on each wafer. Ideally, each device would have the same channel depth, but the variability in gas concentration inside the etching chambers caused some variation in the channel depth between devices. This variation ranged from 88 nm to 103 nm for the slits and 906 nm to 936 nm for the microchannels between different devices. The filtration experiments discussed below used a device with a slit depth of 88 nm and microchannel depth of 906 nm. FIG. 17A is a plot showing the profilometer profile of nanoslits for this device. FIG. 17B is a plot showing the profilometer profile of the microchannel for this device. The integrity of the final fabricated device was further verified using SEM.

The following experiments used two model systems: λ DNA (48.5 kilobase pairs, kbp, available from New England Biolabs, Ipswich, Mass.; radius of gyration about 750 nm) as a prototypical long DNA molecule and 2 kbp DNA sample (also available from New England Biolabs; radius of gyration of about 100 nm) as a model short DNA contaminant. The DNA was stained with YOYO-1 fluorescent dye (available from ThermoFisher Scientific, Waltham, Mass.) at a concentration of 1 dye molecule per 10 base pairs (bp) for λ DNA, and 1 dye molecule per 5 bp for 2 kbp DNA. The stock DNA solution was prepared in 1×TBE (Tris/Borate/Ethylenediaminetetraacetic acid) buffer solution. For the experiments, the sample solution was prepared in 4×TBE buffer supplemented with 3% (w/v) 40 kDa polyvinyl pyrrolidine (available from Sigma-Aldrich Corporation, St. Louis, Mo.) and 6% (v/v) β-mercaptoethanol (BME, available from Sigma-Aldrich Corporation). The final solution for all experiments had a DNA concentration of 3 μg/ml.

The filtration device was mounted on a custom-built chuck that contains reservoirs for buffer solution as well as connections to simultaneously apply the hydrostatic pressure and electric potential at each port. The filtration process for each DNA molecule was recorded with a sCMOS camera (ANDOR Zyla 4.2, available from Andor Technology, Belfast, Ireland) using a 100× (1.4 N.A.) oil immersion objective on an inverted epifluorescence microscope (Leica DMI 4000B, available from Leica Camera AG, Wetzlar, Germany) with a 120 W metal halide source. Micro-manager was programmed to synchronize the stage movement and camera recording during the filtration process. The air pressure and electric potential at each port were independently controlled using a LabVIEW program (National Instruments Corp., Austin, Tex.). For these experiments, all pressure related steps were performed at a gauge pressure of 2.5 kPa. The injection time ($t_3$ in FIG. 3A) was set as 35 seconds, which was sufficient for the filtered DNA to leave the main filtration region and the concentrated DNA to move from the pre-concentration region to the main filtration region. The short pressure pulse ($t_1$ in FIG. 3A) was applied for 2 seconds, with a delay ($t_2$ in FIG. 3A) of 18 seconds between the two pressure pulses. The filtration process was quantified by measuring the decrease in the fluorescence intensity at the slit-channel interface during a filtration cycle. The final percentage decrease in the fluorescence intensity was averaged over two filtration cycles for each filtration condition.

Figure 18A:
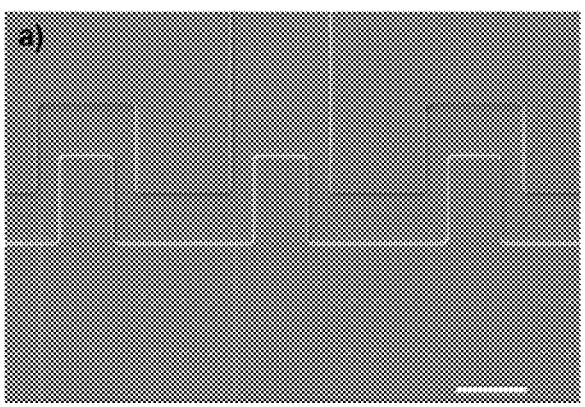
FIG. 18A is a scanning electron microscopy (SEM) image of a first microchannel near the center purge port.
Figure 18B:
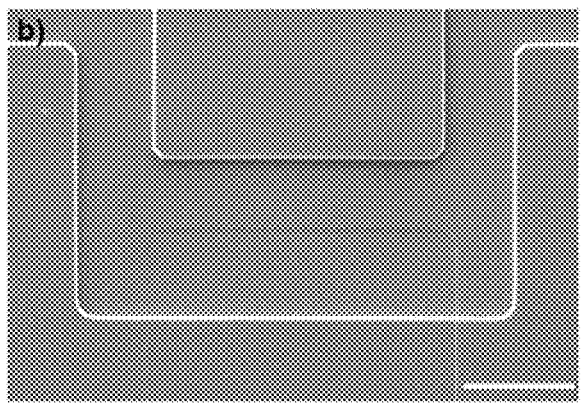
FIG. 18B is a scanning electron microscopy (SEM) image of the final slit-channel interface that provides the entropic barrier for filtration.

FIGS. 18A and 18B show scanning electron microscopy (SEM) images of a section of a fabricated device. The scale bar is 20 micrometers in FIG. 18A and 10 micrometers in FIG. 18B. The serpentine shape of the microchannels was designed to produce a potential drop within the channels in a compact geometry. Note that the channel potential drop produces the focusing predicted by FIGS. 7A and 7B and the COMSOL model.

Figure 18C:
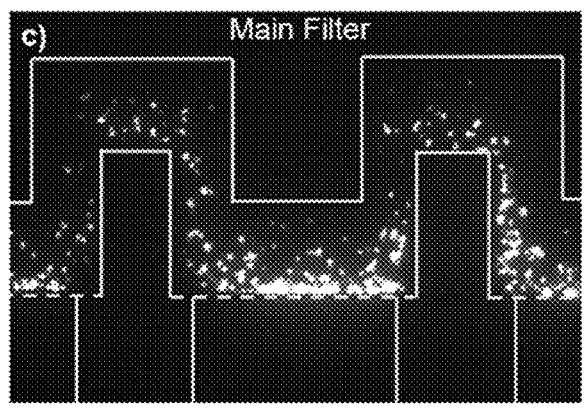
FIG. 18C is a fluorescent image of λ DNA molecules in a main filtration region near a third slit just after completion of an injection cycle.
Figure 18D:
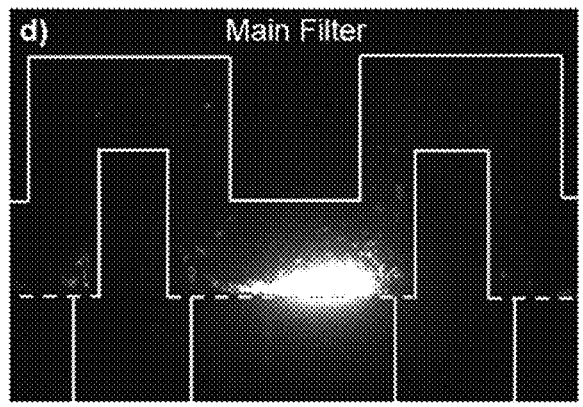
FIG. 18D is a fluorescent image of λ DNA molecules in a main filtration region near a third slit just before completion of a filtration cycle.

FIGS. 18C and 18D show the basic operation of the device. In FIG. 18C, the main filtration zone is shown as it is filled with λ DNA molecules just after the injection cycle of FIGS. 3A and 3B. FIG. 18D shows how these DNA molecules are concentrated at the completion of the filtration cycle of FIGS. 3A and 3B. The pressure pulse for the DNA oscillation in the filtration cycle shifted the focusing of DNA in the direction of the pressure pulse, i.e. the DNA mostly focused on the third slit rather than the fourth slit predicted by the purely electrophoretic model in FIG. 7B. However, the pressure pulse does not cause the DNA to jump to a new channel-slit interface during the filtration step. Rather, the pressure pulse simply mixes the DNA at the interface to aid in filtration.

One possible concern in our device is the possibility of migration of the DNA away from the walls due to the shear flow produced by the pressure pulses. However, any significant impact of lateral migration was not observed during the filtration process. This outcome may be attributed to two aspects of the device. First, during the filtration cycle, both the filtration zone and the concentration zone operate predominately under the influence of the electric field, with a small pressure pulse used to mix the DNA within the potential well created by the non-uniform electric field within the channel. These pressure pulses (duration $t_1$=2 seconds) may not be long enough to develop a steady-state depletion layer near the wall. Second, as the DNA are focused near the slit-channel interface and form a DNA plug (as shown in FIGS. 18C and 18D), the higher solution viscosity near the wall (created by the concentrated DNA plug) and screening of hydrodynamics near the wall at finite concentration should further reduce the migration effect. While lateral migration is suspected to have a negligible effect on separation, enhancing its role could aid the filtration process. Based on theory, the flow-induced depletion length will be larger for long DNA as compared to the short DNA. This implies that the long DNA should move away from the wall more than the short DNA, and thus reduce their escape attempt frequency at the slit entrance. The net effect is to increase the β for short DNA when compared to long DNA and assist the filtration.

The device was designed for proof-of-concept experiments using pure 2 kbp and 48.5 kbp DNA separately. This separation is considerably more challenging than the targeted application in genome mapping, where the large DNA molecules are in excess of 150 kbp, and thus provides a very stringent test of the principles underlying the filtration device. These experiments, albeit more labor-intense than studying a mixture, allow us to quantify the filtration of short and long DNA molecules, respectively, without concern about spectral overlap and possible exchange of fluorescent dyes between molecules in a two-color experiment.

The device was designed with a slit height close to the radius of gyration of the short DNA, but much smaller than that of the long DNA. The configurational degrees of freedom for the short DNA are not significantly reduced by entry into the shallow region, implying that they do not have much of a partition between the shallow and the deep region and that a is relatively small. On the other hand, the long DNA molecules encounter a configurational entropy barrier associated with the deformation of the molecule for it to enter the slit region, whereupon α is relatively large. It is thus expected to observe different values of β for these two species. The slit height is an important aspect in the device design, and it can be tuned to set the filtration cut-off at different molecular weights.

Like most filtration processes, the system described herein entails a tradeoff between selectivity and recovery of the filtrate. From the equations for τ and β, our discussion of device tunability suggests two different approaches to alter β: (i) changing the filtration voltage, which affects r through changes in the electric field in the slits, $E_s$; and (ii) changing the filtration time, $t_4$. Each of these approaches is investigated separately in what follows.

Figure 19A:
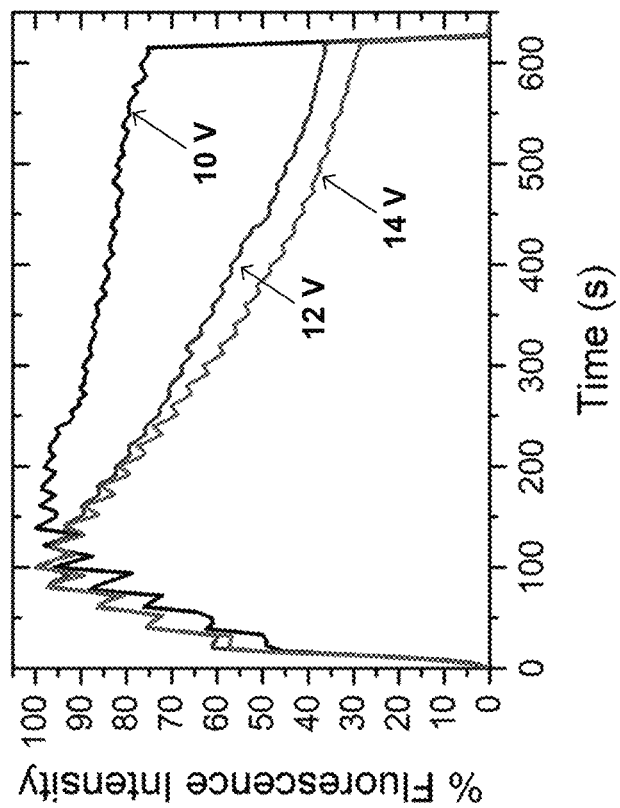
FIGS. 19A and 19B are plots of percentage recovery of DNA for a filtration time of 600 seconds at different filtration voltages for 2 kbp and λ DNA molecules, respectively.
Figure 19B:
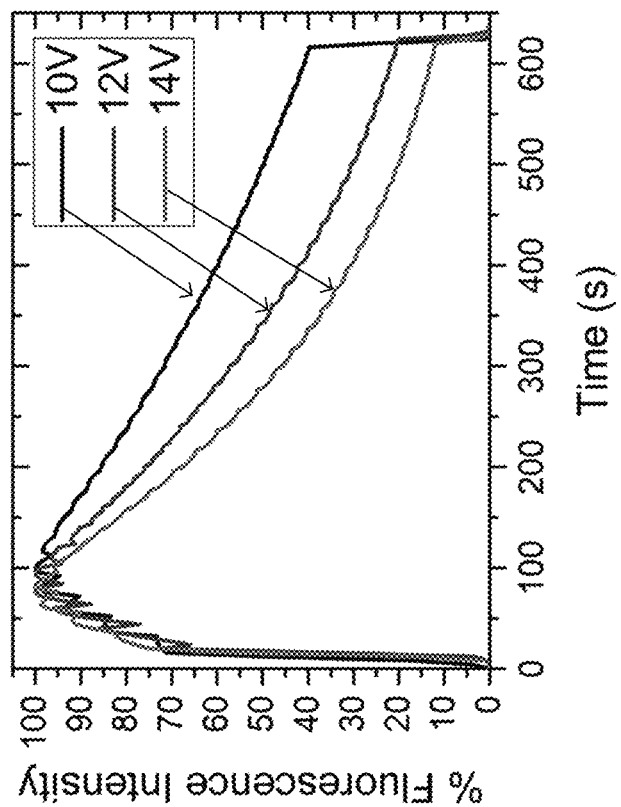

The performance of the device at filtration voltages of 10 V, 12 V, and 14 V was investigated while fixing the filtration time at 600 seconds. FIGS. 19A and 19B show how the fluorescence intensity at the slit-channel interface (FIG. 18D) changes as a function of time for these conditions using either 2 kbp DNA (FIG. 19A) or λ DNA (FIG. 19B). These plots present the average of the fluorescence intensity over injection/filtration cycles in a single experiment, and these data correspond to the fluorescence intensity in the main filtration zone of FIG. 7A. The main filtration zone was studied, rather than the pre-concentration zone, because the initial condition for the main filtration zone is the total amount of DNA to be filtered; for the pre-concentration zone, the filtration step involves a combination of filtration and continued injection and concentration of DNA from the loading reservoir, making it challenging to deconvolve the role of these two effects on the total fluorescence intensity.

It is clear from the data in FIGS. 19A and 19B that the fluorescence intensity of the shorter DNA is decreasing as it is filtered through the device. In contrast, the longer DNA are retained at the slit. However, as noted in the context of the equation for τ, there is a finite escape time for the long DNA. Thus, as the filtration is run for a longer time, the longer DNA eventually begin to escape over the barrier.

To convert the data in FIGS. 19A and 19B into a quantitative metric for the device performance, the filtration efficiency was defined to be proportional to the percentage of DNA (% fluorescence intensity) left in the main filtration zone at the end of the filtration cycle. For example, in case of 12 V, more than 40% of long DNA was recovered as compared to 20% recovery of short DNA when operated at the same condition.

The experiment shown in FIGS. 19A and 19B was repeated multiple times. The results are summarized in Table 1.

TABLE 1

Percentage recovery of DNA molecules different trials and averaged DNA recovery for two DNA types as well as the selectivity of filtration at 600 second filtration time for different filtration voltages. The electric field strength in slit 3 was calculated for each filtration voltage using the resistor model shown in FIGS. 7A and 7B.

| Filtration Voltage | Electric field (V/cm) | Recovery (%) Long DNA | Recovery (%) Short DNA | Average Recovery (%) | Selectivity Ratio |
|---|---|---|---|---|---|
| 10 V | 8.75 | 60, 75, 46 | 30, 40 | 60 (long) 35 (short) | 1.7 |
| 12 V | 10.50 | 58, 37, 45 | 20, 20 | 41 (long) 20 (short) | 2.1 |
| 14 V | 12.24 | 41, 29, 36 | 8, 12 | 35 (long) 10 (short) | 3.5 |

When the separation was performed on different days for the same operating conditions, the percentage recovery of long DNA between trials varied by up to 15%. The corresponding day-to-day variation for small DNA molecules was 5% or less. The variability in filtration, however, decreased with increasing filtration voltage. As such, the variability in the filtration of the large DNA may be attributed to the fluctuation in the mobility of DNA and the frequency of barrier hopping at relatively low electric fields. Previous studies have also reported mobility variations as large as 15%. These works tend to suggest that the variation in the mobility is more prominent at low electric fields and in the buffer solution with PVP. Both of these conditions exist in the system.

The amount of short DNA removed from the solution increased from 60% to 90% on increasing the filtration voltage from 10 V to 14 V. This, in turn, increases the selectivity of filtration of short DNA as compared to long DNA in Table 1. But the improved selectivity comes at the expense of losing more λ DNA molecules with increasing filtration voltage. The recovery of λ DNA decreased from 60% to 40% with an increase in the filtration from 10 V to 14 V, consistent with the discussion of device tunability via the equations for τ and β.

Figure 20A:
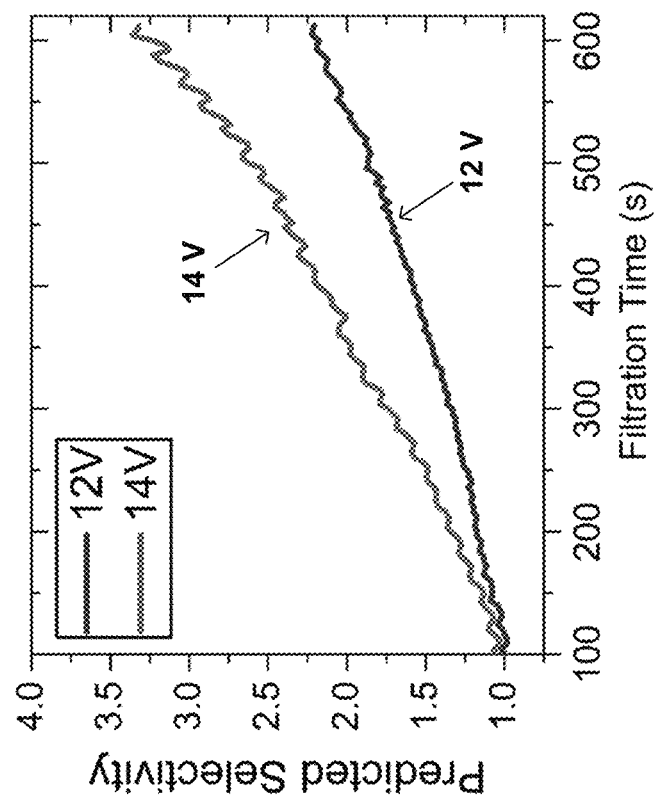
FIG. 20A is a plot of percentage recovery of DNA for a filtration voltage of 12 V at different filtration times for (i) λ DNA molecules and (ii) 2 kbp DNA molecules.

The second approach to control β is to control the duration of the filtration cycle. FIG. 20A shows the filtration profile of 2 kbp and λ DNA, separately, for two different filtration times at a filtration voltage of 12 V. The fluorescence intensity profiles for the two different filtration times nicely overlap on each other for both DNA sizes, indicating a high reproducibility within a given experiment. As a result, a filtration profile obtained for a large value of $t_4$ should predict the filtration efficiency for a shorter filtration time. Table 2 summarizes the effectiveness of this approach, using the data obtained for a 600 second filtration time to predict the result for a 450 second experiment. The additional data for a filtration voltage of 14 V appear as FIGS. 21A and 21B. Despite the variation in the mobility for different trials that was observed in Table 1, a similar recovery and overall filtration curves were obtained for the two different filtration times.

TABLE 2

Percent recovery of individual DNA molecules for 600 second and 450 second filtration as well as the anticipated recovery at 450 s based on the filtration profile from 600 second filtration time. The electric field strength in slit 3 was calculated for each filtration voltage using the resistor model shown in FIGS. 7A and 7B.

| | Filtration voltage (V) | Electric field (V/cm) | Recovery (%) 600 seconds | Recovery (%) 450 seconds (predicted) | Recovery (%) 450 seconds (actual) |
|---|---|---|---|---|---|
| 2 kbp DNA | 12 | 10.50 | 20 | 35 | 36 |
| 2 kbp DNA | 14 | 12.24 | 12 | 25 | 25 |
| λ DNA | 12 | 10.50 | 45 | 59 | 58 |
| λ DNA | 14 | 12.24 | 37 | 48 | 54 |

Figure 20B:
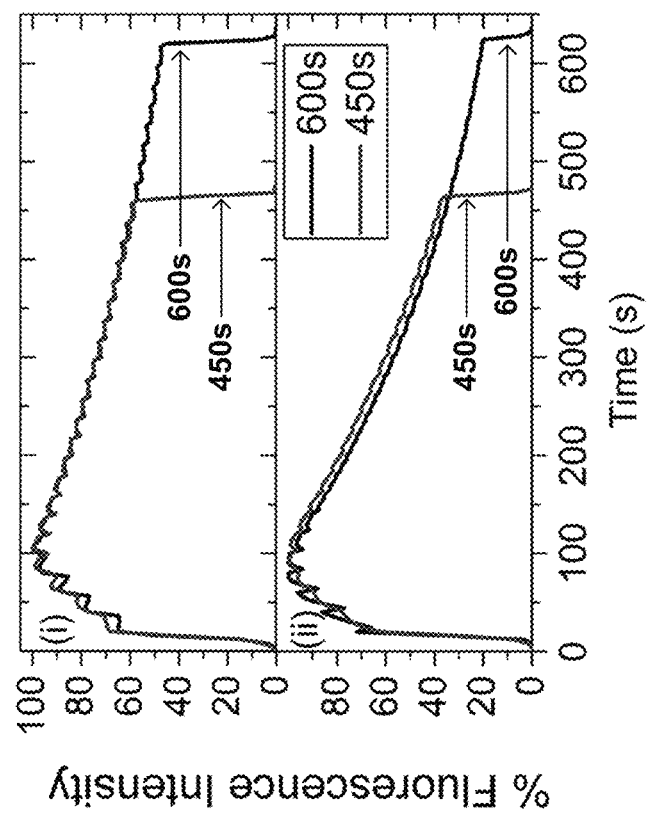
FIG. 20B is a plot of predicted selectivity profiles for filtration of λ DNA molecules over 2 kbp DNA molecules for different filtration voltages.
Figure 21A:
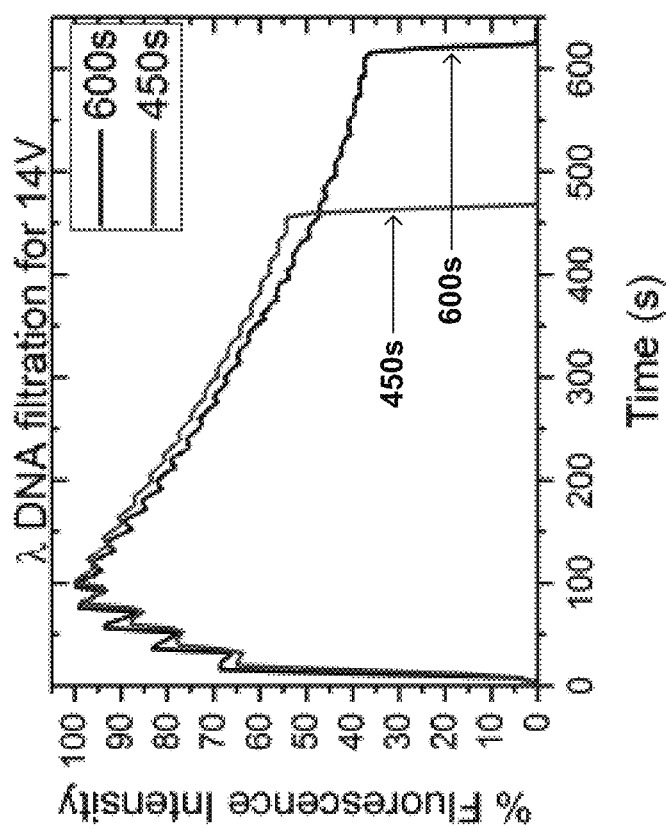
FIG. 21A is a plot of percentage recovery of DNA for a filtration voltage of 14 V at different filtration times for 2 kbp DNA molecules.
Figure 21B:
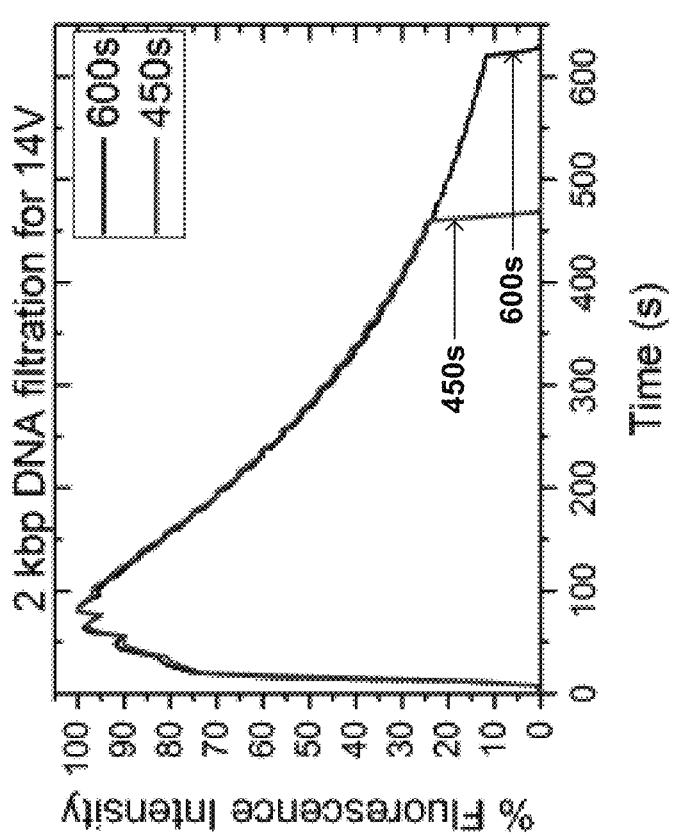
FIG. 21B is a plot of percentage recovery of DNA for a filtration voltage of 14 V at different filtration times for λ kbp DNA molecules.
Figure 22B:
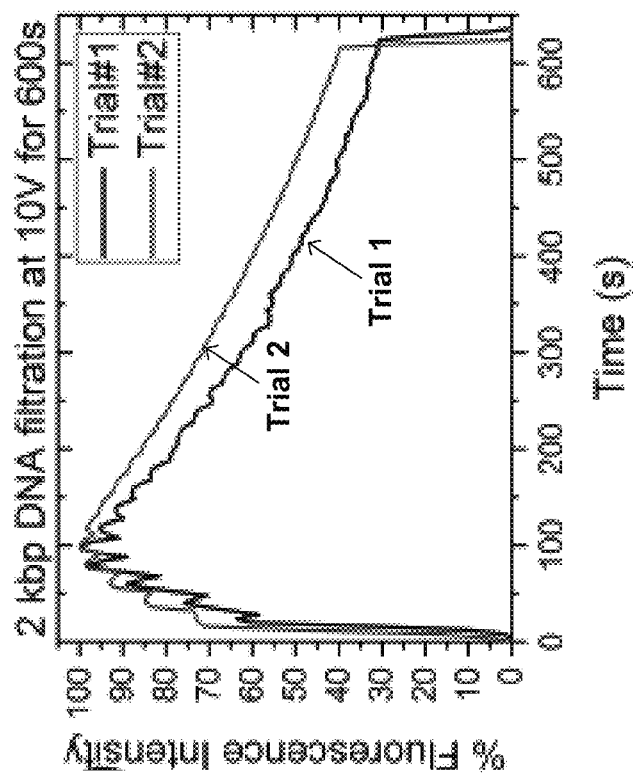
FIGS. 22A-22F are plots of percentage recovery of DNA for a filtration time of 600 seconds at different filtration voltages for λ kbp DNA molecules and 2 kbp DNA molecules.
Figure 22A:
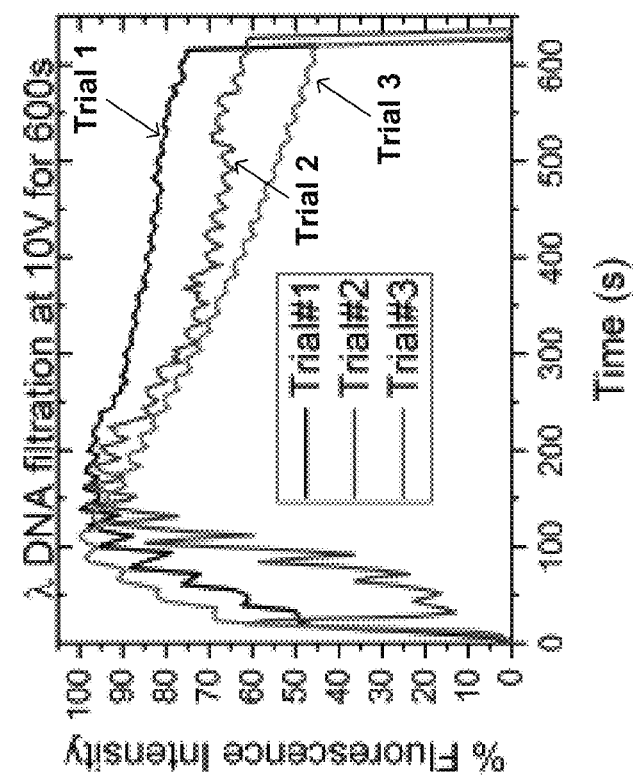
Figure 22D:
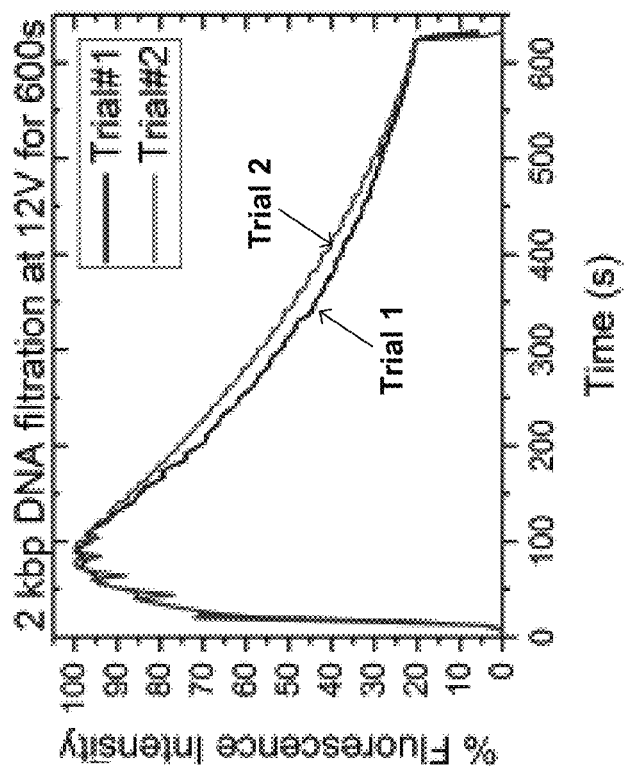
Figure 22C:
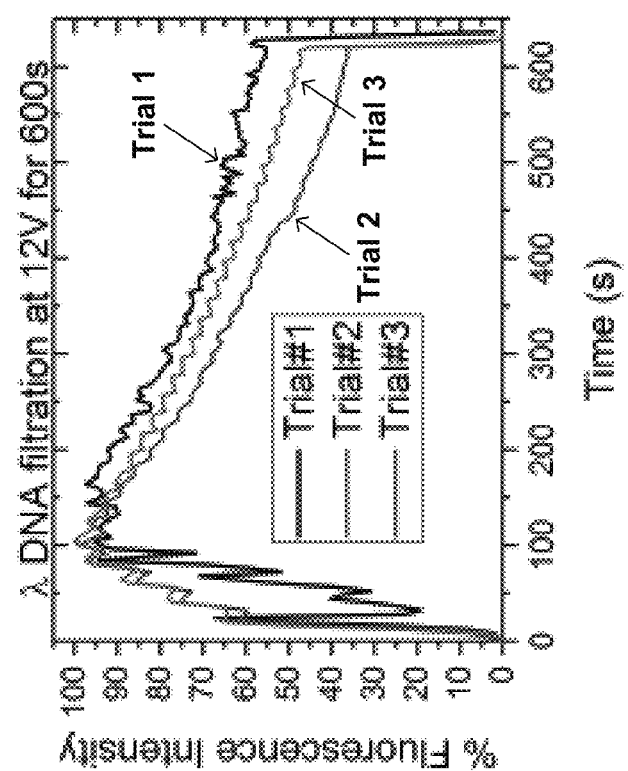
Figure 22F:
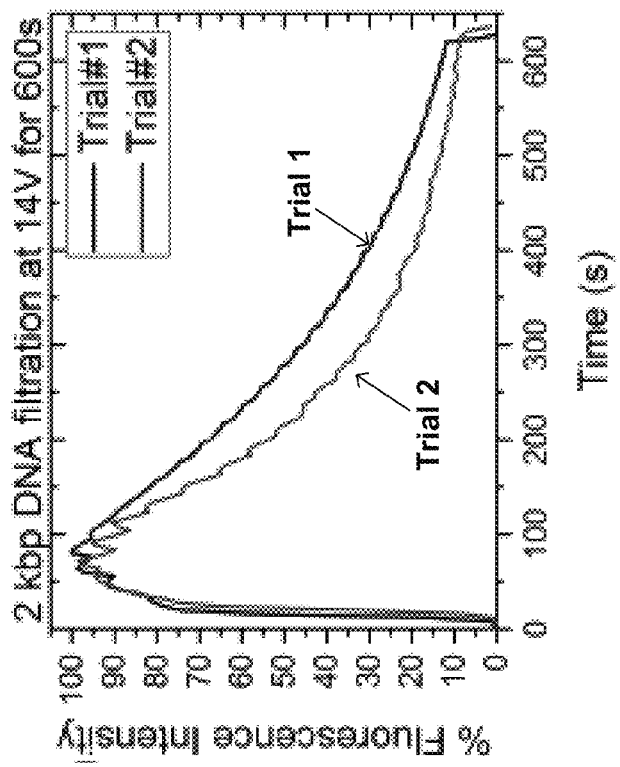
Figure 22E:
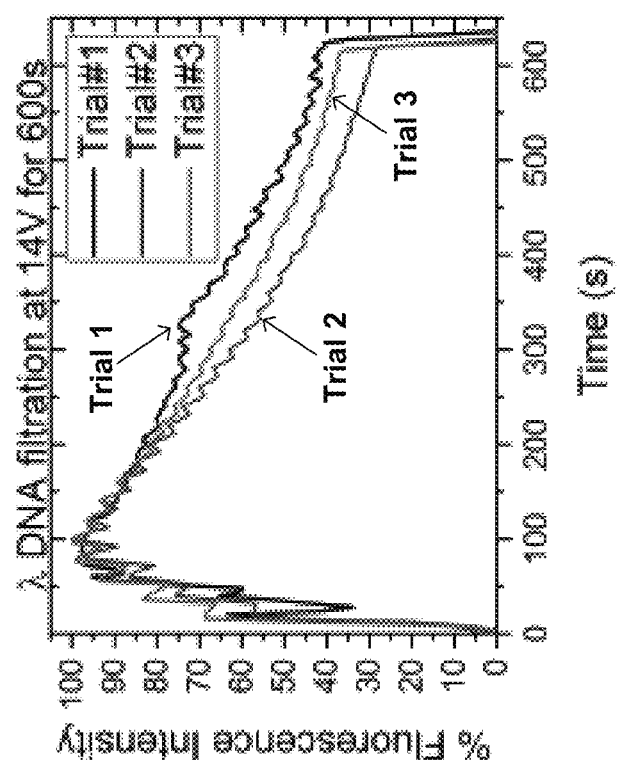

Having demonstrated separately the two approaches for controlling β, i.e. filtration voltage and filtration time, the predicted selectivity profiles were predicted and are shown in FIG. 20B for the filtration of λ and 2 kbp DNA at different filtration times for 12 V and 14 V, based on the data presented in FIGS. 22A-22F and Table 1. The data in FIG. 20B were obtained by taking the ratio of average fluorescence intensity for λ and 2 kbp DNA molecules at different filtration times. For each DNA size, the average fluorescence intensity for particular filtration voltage is computed from the ensemble of all the independent trials.

FIG. 20B shows that for a particular filtration time, the selectivity increases with increasing filtration voltage and there is a higher selectivity for longer filtration times at a fixed filtration voltage. There is a small difference between the selectivity values at 600 seconds in FIG. 20B and Table 1. This difference arises from the need to manually align the filtration profiles between different experiments for all filtration times to compute the average intensity profiles and selectivity. Overall, these results demonstrate the ability of the system to tune the filtration quality by balancing between the selectivity and recovery efficiency depending upon the need of the application.

Various examples have been described. These and other examples are within the scope of the following claims.

What is claimed is:
1. A molecular filter comprising:
a substrate defining:
a first channel;
a second channel substantially parallel to the first channel;
a filtration stage comprising a plurality of slits extending substantially perpendicular to the first channel and the second channel from the first channel to the second channel, wherein the first channel and the plurality of slits define a channel-slit interface acting as an entropic filter, wherein a respective cross-sectional area of each respective slit of the at least one slit in a plane perpendicular to a long axis of the respective slit is smaller than a cross-sectional area of the first channel in a plane perpendicular to a long axis of the first channel;
at least one inlet port fluidically coupled to the first channel;
at least one recovery port fluidically coupled to the first channel;
at least one purge port fluidically coupled to the first channel at or near a midpoint of the filtration stage; and
at least one filtrate port fluidically coupled to the second channel;
a voltage source coupled to the at least one inlet port and the at least one filtrate port;
a fluid source fluidically coupled to the at least one inlet port and the at least one purge port; and
a controller, wherein the controller is configured to:
during an introduction phase, control the voltage source to not apply a voltage to the at least one inlet port and the at least one filtrate port and control the fluid source to apply pressure to the at least one inlet port and the at least one purge port to push a sample in the at least one inlet port into the first channel; and
during a filtration phase, control the voltage source to apply a constant voltage between the at least one inlet port and the at least one filtrate port and control the fluid source to apply an oscillating pressure to the at least one inlet port and the at least one purge port.

2. The molecular filter of claim 1, wherein the at least one inlet port and the at least one purge port are configured to be fluidically coupled to a fluid source, and wherein the recovery port is not fluidically coupled to a fluid source.

3. The molecular filter of claim 1, wherein the at least one inlet port, the at least one purge port, and the at least one filtrate port are configured to be electrically connected to a voltage source, and wherein the recovery port is not coupled to a voltage source.

4. The molecular filter of claim 1, wherein:
the at least one inlet port comprises a single inlet port;
the at least one recovery port comprises a single recovery port;
the at least one purge port comprises a first purge port and a second purge port;
the single inlet port is fluidically connected to a first end of the first channel;
the first purge port is fluidically connected to a second end of the first channel;
the first end is opposite the second end;
the second purge port is fluidically connected to an intermediate portion of the first channel; and
the single recovery port is fluidically connected to the first channel at a location between the second end and the intermediate portion.

5. The molecular filter of claim 1, wherein the combination of the constant voltage and the oscillating pressure causes filtride of the sample to concentrate at one or more portions of the channel-slit interface between the first channel and the plurality of slits.

6. The molecular filter of claim 4, wherein the plurality of slits fluidically couple the first channel to the second channel in parallel, and wherein the one or more portions of the channel-slit interface are symmetric about the midpoint of the filtration stage.

7. The molecular filter of claim 5, wherein the filtride comprises relatively long chain DNA, and wherein the filtrate comprises at least one of relatively short chain DNA, RNA, charged free dye molecules, or other impurities smaller than the relatively long chain DNA.

8. The molecular filter of claim 5, wherein the controller is configured to cause the introduction phase and the filtration phase to repeat in an alternating pattern.

9. The molecular filter of claim 1, wherein the molecular filter is a short-pass filter for recovering relatively long chain DNA molecules.

10. The molecular filter of claim 1, wherein respective interfaces between the first channel and the respective slits of the at least one slit comprise entropic traps.

11. The molecular filter of claim 1, wherein at least one of the first channel or the second channel defines a depth between about 100 nm and about 10,000 nm.

12. The molecular filter of claim 1, wherein the plurality of slits define a height between about 1 nm and about 500 nm.

13. The molecular filter of claim 1, wherein a height of the plurality of slits is selected to be smaller than a radius of gyration of a long chain DNA molecule to be isolated using the molecular filter and larger than a radius of gyration of a short chain DNA molecule to be removed using the molecular filter.

14. A filter system comprising:
   a substrate defining:
      a first channel;
      a second channel;
      a first filtration stage comprising a first plurality of slits extending substantially perpendicular to the first channel and the second channel from the first channel to the second channel, wherein the first channel and the first plurality of slits define a first channel-slit interface acting as a first entropic filter, wherein a respective cross-sectional area of each respective slit of the first stage in a plane perpendicular to a long axis of the respective slit is smaller than a cross-sectional area of the first channel in a plane perpendicular to a long axis of the first channel;
      a first purge channel fluidically coupled to the first channel at or near a midpoint of the first filtration stage;
      a second filtration stage downstream of the first filtration stage along the first channel, wherein the second filtration stage comprises a second plurality of slits extending substantially perpendicular to the first channel and the second channel from the first channel to the second channel, wherein a respective cross-sectional area of each respective slit of the second filtration stage in a plane perpendicular to a long axis of the respective slit is smaller than a cross-sectional area of the first channel in a plane perpendicular to a long axis of the first channel;
      a second purge channel fluidically coupled to the first channel at or near a midpoint of the second stage;
      at least one inlet port fluidically coupled to the first channel upstream of the first stage along the first channel;
      at least one recovery port fluidically coupled to the first channel downstream of the second stage along the first channel; and
   at least one filtrate port fluidically coupled to the second channel;
   a voltage source coupled to the at least one inlet port and the at least one filtrate port;
   a fluid source fluidically coupled to the at least one inlet port; and
   a controller, wherein the controller is configured to:
      during an introduction phase, control the voltage source to not apply a voltage to the at least one inlet port and the at least one filtrate port and control the fluid source to apply pressure to the at least one inlet port to push a sample in the at least one inlet port into the first channel; and
      during a filtration phase, control the voltage source to apply a constant voltage between the at least one inlet port and the at least one filtrate port and control the fluid source to apply an oscillating pressure to the at least one inlet port.

* * * * *